US011490966B2

(12) United States Patent
Roche et al.

(10) Patent No.: US 11,490,966 B2
(45) Date of Patent: Nov. 8, 2022

(54) METHOD AND SYSTEM FOR MODELING PREDICTIVE OUTCOMES OF ARTHROPLASTY SURGICAL PROCEDURES

(71) Applicant: EXACTECH, INC., Gainesville, FL (US)

(72) Inventors: Christopher Roche, Gainesville, FL (US); Vikas Kumar, Gainesville, FL (US); Steven Overman, Gainesville, FL (US); Ankur Teredesai, Gainesville, FL (US); Howard Routman, Gainesville, FL (US); Ryan Simovitch, Gainesville, FL (US); Pierre-Henri Flurin, Gainesville, FL (US); Thomas Wright, Gainesville, FL (US); Joseph Zuckerman, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 0 days.

(21) Appl. No.: 17/233,152

(22) Filed: Apr. 16, 2021

(65) Prior Publication Data
US 2021/0322100 A1    Oct. 21, 2021

Related U.S. Application Data

(60) Provisional application No. 63/011,871, filed on Apr. 17, 2020.

(51) Int. Cl.
*A61B 34/10* (2016.01)
*G16H 10/60* (2018.01)
(Continued)

(52) U.S. Cl.
CPC .............. *A61B 34/10* (2016.02); *A61B 90/37* (2016.02); *G06N 20/00* (2019.01); *G16H 10/60* (2018.01);
(Continued)

(58) Field of Classification Search
CPC ... A61B 34/10; A61B 90/37; A61B 2034/104; A61B 2090/374; A61B 2090/3762;
(Continued)

(56) References Cited

U.S. PATENT DOCUMENTS

2010/0087927 A1    4/2010 Roche et al.
2016/0350506 A1*  12/2016 Kohli ..................... G16H 50/50
(Continued)

OTHER PUBLICATIONS

Levy, Jonathan C., Moses T. Ashukem, and Nathan T. Formaini. "Factors predicting postoperative range of motion for anatomic total shoulder arthroplasty." Journal of shoulder and elbow surgery 25.1 (2016): 55-60. (Year: 2016).*

(Continued)

*Primary Examiner* — Amanda Lauritzen Moher
(74) *Attorney, Agent, or Firm* — Greenberg Traurig, LLP

(57) ABSTRACT

An apparatus includes a processor and a non-transitory memory. The processor is configured to receive pre-operative patient specific data. The pre-operative patient specific data is inputted to a first machine learning model to determine a first predicted post-operative joint performance data output including first predicted post-operative outcome metrics. A reconstruction plan of the joint of the patient is generated based on a medical image of the joint, and at least one arthroplasty surgical parameter obtained from the user. The at least one arthroplasty surgical parameter is inputted into a second machine learning model to determine a second predicted post-operative joint performance data output including second predicted post-operative outcome metrics. The second predicted post-operative joint performance data output is updated to include an arthroplasty surgery recommendation, in response to the user varying the at least one arthroplasty surgical parameter, before the arthroplasty surgery, during the arthroplasty surgery, or both.

22 Claims, 38 Drawing Sheets

(51) Int. Cl.
*G16H 20/40* (2018.01)
*G06N 20/00* (2019.01)
*A61B 90/00* (2016.01)

(52) U.S. Cl.
CPC ........ *G16H 20/40* (2018.01); *A61B 2034/104* (2016.02); *A61B 2090/374* (2016.02); *A61B 2090/3762* (2016.02)

(58) Field of Classification Search
CPC ........ G16H 20/40; G16H 10/60; G16H 50/50; G16H 50/30; G16H 10/20; G16H 30/40; G16H 40/67; G16H 50/20; G06N 20/00; G06N 20/10; G06N 20/20; G06N 3/0445; G06N 3/0454; G06N 5/003; G06N 7/005
See application file for complete search history.

(56) References Cited

U.S. PATENT DOCUMENTS

| | | | |
|---|---|---|---|
| 2017/0061375 A1 | 3/2017 | Laster et al. | |
| 2018/0330800 A1* | 11/2018 | Bogue | G16H 15/00 |
| 2020/0243199 A1* | 7/2020 | Farley | G16H 50/70 |
| 2021/0005321 A1* | 1/2021 | Hwang | G16H 50/50 |

OTHER PUBLICATIONS

Lopez et al. "Artificial Learning and Machine Learning Decision Guidance Applications in Total Hip and Knee Arthroplasty: A Systematic Review." Arthroplasty Today 11(7697):103-112. Oct. 2021.*

Lambrechts et al. "Artificial Intelligence Based Patient-Specific Preoperative Planning Algorithm for Total Knee Arthroplasty." Front. Robot. AI 9: 840282. Mar. 2022.*

International Search Report and Written Opinion from International Application No. PCT/US2021-027782 dated Aug. 3, 2021.

* cited by examiner

| Outcome Measure | M (CI) | SCB |
|---|---|---|
| ASK (ISA, TSA) | 13.6 (17.0, 10.3) | 31.5 (37.6, 25.9) |
| TSK (ISA, TSA) | 8.7 (10.5, 7.0) | 12.6 (15.0, 10.4) |
| Constant (ISA, TSA) | 5.7 (12.8, -0.3) | 19.1 (25.4, 13.6) |
| Global Shoulder Function (ISA, TSA) | 1.4 (1.7, 1.0) | 3.1 (3.9, 2.4) |
| VAS Pain (ISA, TSA) | 1.6 (2.7, 1.4) | 3.2 (3.8, 2.6) |
| Abduction (ISA, TSA) | 7.0 (13.9, -1.9) | 28.5 (36.1, 19.6) |
| Forward Elevation (ISA, TSA) | 12.0 (23.1, -2.9) | 35.4 (45.5, 22.3) |
| External Rotation (ISA, TSA) | 3.0 (14.5, -5.3) | 11.7 (20.1, 3.6) |

FIG. 5

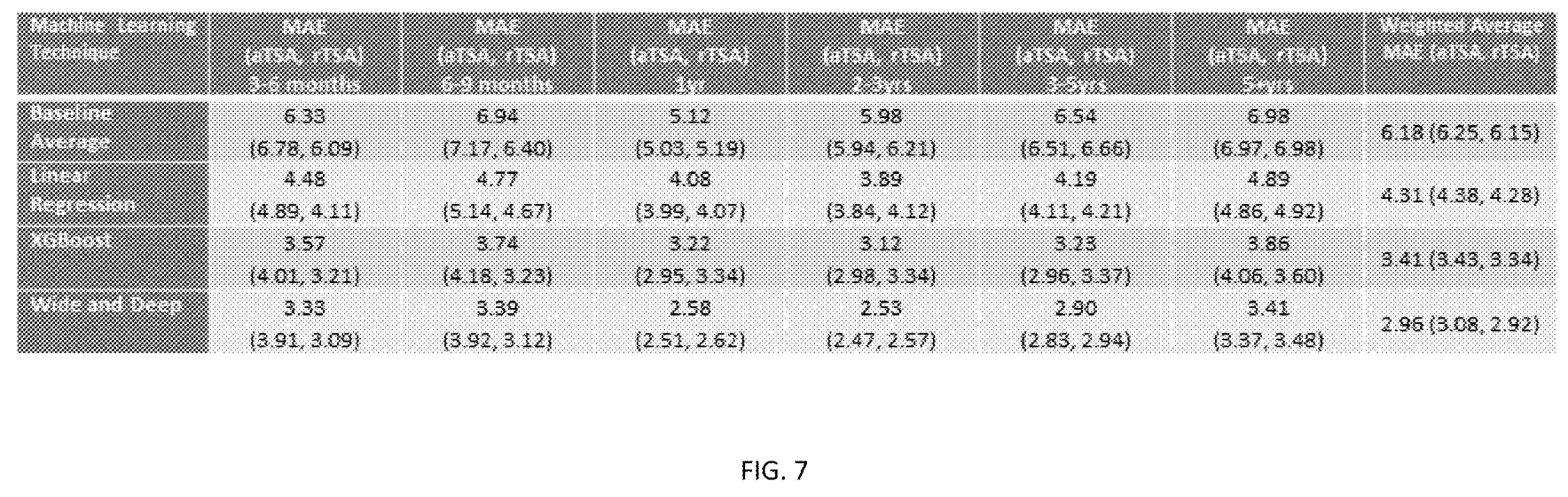

| Sampling Location | Mid Canning (Centre of Canning) | Mid Canning (Riverside) | SJBR Stormdrain (Outlet) | Mid Canning (Riverside) | Mid Canning (Polo Club) | Mid Canning (Zoo) |
|---|---|---|---|---|---|---|
| Highest Concentration | 6.33 | 6.94 | 5.12 | 5.98 | 6.54 | 6.98 |
| | (6.78, 6.09) | (7.17, 6.40) | (5.03, 5.19) | (5.94, 6.21) | (6.51, 6.66) | (6.97, 6.98) |
| Lowest Concentration | 4.48 | 4.77 | 4.08 | 3.89 | 4.19 | 4.89 |
| | (4.89, 4.11) | (5.14, 4.67) | (3.99, 4.07) | (3.84, 4.12) | (4.11, 4.21) | (4.86, 4.92) |
| Median Concentration | 3.57 | 3.74 | 3.22 | 3.12 | 3.23 | 3.86 |
| | (4.01, 3.21) | (4.18, 3.23) | (2.95, 3.34) | (2.98, 3.34) | (2.96, 3.37) | (4.06, 3.60) |
| Average Concentration | 3.33 | 3.39 | 2.58 | 2.53 | 2.90 | 3.41 |
| | (3.91, 3.09) | (3.92, 3.12) | (2.51, 2.62) | (2.47, 2.57) | (2.83, 2.94) | (3.37, 3.48) |
| Concentration Count | | | | | | 6.18 (6.25, 6.15) |
| | | | | | | 4.31 (4.36, 4.28) |
| | | | | | | 3.41 (3.43, 3.34) |
| | | | | | | 2.96 (3.08, 2.92) |

FIG. 7

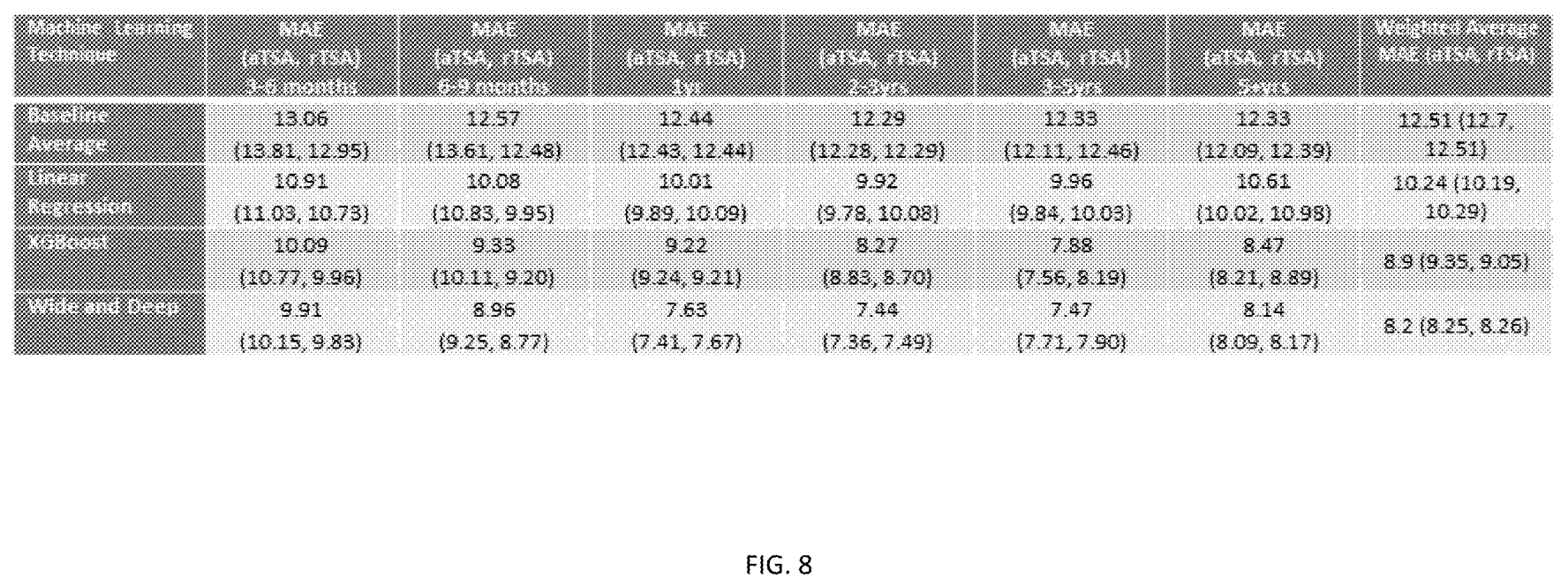

| | | | | | | |
|---|---|---|---|---|---|---|
| | 13.06 (13.81, 12.95) | 12.57 (13.61, 12.48) | 12.44 (12.43, 12.44) | 12.29 (12.28, 12.29) | 12.33 (12.11, 12.46) | 12.33 (12.09, 12.39) | 12.51 (12.7, 12.51) |
| | 10.91 (11.03, 10.73) | 10.08 (10.83, 9.95) | 10.01 (9.89, 10.09) | 9.92 (9.78, 10.08) | 9.96 (9.84, 10.03) | 10.61 (10.02, 10.98) | 10.24 (10.19, 10.29) |
| | 10.09 | 9.33 | 9.22 | 8.27 | 7.88 | 8.47 | |
| | 10.77 (9.96) | 10.11 (9.20) | 9.24 (9.21) | 8.83 (8.70) | 7.56 (8.19) | 8.21 (8.89) | 8.9 (9.35, 9.05) |
| | 9.91 | 8.96 | 7.63 | 7.44 | 7.47 | 8.14 | |
| | 10.15 (9.83) | 9.25 (8.77) | 7.41 (7.67) | 7.36 (7.49) | 7.71 (7.90) | 8.09 (8.17) | 8.2 (8.25, 8.26) |

FIG. 8

| | MALE TRAINED | MALE CHALLENGED UNTRAINED | MALE UNTRAINED | FEMALE CHALLENGED | FEMALE UNTRAINED | MALE CHALLENGED | FEMALE CHALLENGED |
|---|---|---|---|---|---|---|---|
| | 1.60 (1.51, 1.69) | 1.64 (1.55, 1.73) | 1.46 (1.54, 1.44) | 1.48 (1.53, 1.47) | 1.44 (1.42, 1.47) | 1.72 (1.77, 1.70) | 1.55 (1.55, 1.57) |
| | 1.52 (1.46, 1.65) | 1.58 (1.49, 1.67) | 1.42 (1.49, 1.36) | 1.42 (1.48, 1.39) | 1.35 (1.39, 1.30) | 1.64 (1.69, 1.58) | 1.48 (1.5, 1.48) |
| | 1.42 (1.32, 1.51) | 1.45 (1.39, 1.53) | 1.34 (1.44, 1.18) | 1.37 (1.43, 1.31) | 1.17 (1.18, 1.15) | 1.47 (1.49, 1.44) | 1.37 (1.38, 1.34) |
| | 1.32 (1.33, 1.49) | 1.39 (1.38, 1.50) | 1.31 (1.39, 1.24) | 1.35 (1.44, 1.30) | 1.02 (1.09, 1.01) | 1.39 (1.41, 1.35) | 1.3 (1.35, 1.31) |

| Compound Name | Batch 1 (Technique 1) | Batch 2 (Technique 2) | Batch 3 (Technique 3) | Batch 4 (Technique 4) | Batch 5 (Technique 5) |
|---|---|---|---|---|---|
| Compound 1 | 24.89 (24.94, 24.88) | 24.33 (24.49, 24.03) | 22.64 (22.74, 22.35) | 20.87 (20.01, 22.02) | 21.42 (21.13, 22.67) | 23.71 (23.97, 23.21) | 23.01 (22.91, 23.24) |
| Compound 2 | 22.42 (22.58, 22.37) | 22.28 (22.41, 22.12) | 21.02 (21.44, 20.96) | 18.62 (17.68, 20.13) | 19.12 (18.96, 19.44) | 19.12 (18.96, 19.44) | 20.59 (20.53, 20.9) |
| Compound 3 | 20.45 (20.50, 20.43) | 20.25 (20.39, 20.03) | 17.38 (17.93, 17.02) | 15.37 (14.95, 17.51) | 15.22 (15.17, 15.26) | 15.67 (16.14, 15.03) | 17.6 (18.03, 17.81) |
| Compound 4 | 20.43 (20.54, 20.33) | 20.21 (20.30, 20.93) | 17.14 (17.81, 17.03) | 15.14 (14.26, 17.04) | 15.09 (15.01, 15.16) | 15.36 (15.85, 14.94) | 17.45 (17.52, 17.79) |

FIG. 12

| | GPU | Titan | Ours w/o sw | Ours w/ sw | Cloud | Edge |
|---|---|---|---|---|---|---|
| | 15.64 (15.49, 15.72) | 15.93 (15.88, 15.99) | 15.63 (15.64, 15.22) | 15.46 (15.98, 14.31) | 16.98 (17.23, 16.71) | 16.99 (17.94, 16.77) |
| | 13.41 (13.38, 13.44) | 13.92 (13.83, 14.14) | 13.89 (14.22, 13.13) | 13.74 (14.18, 12.92) | 14.55 (14.98, 13.88) | 13.93 (14.64, 13.07) |
| | 12.26 (12.18, 12.32) | 12.85 (13.09, 12.62) | 12.71 (13.89, 12.03) | 11.98 (13.04, 11.63) | 12.18 (12.87, 11.65) | 10.31 (11.05, 9.24) |
| | 11.49 (11.24, 11.73) | 11.93 (12.42, 11.77) | 11.92 (12.59, 11.48) | 11.26 (12.12, 11.01) | 11.94 (12.35, 11.31) | 10.03 (10.84, 9.09) |
| | | | | | | 11.5 (11.94, 11.21) |
| | | | | | | 12.15 (13.08, 11.74) |
| | | | | | | 13.85 (14.12, 13.4) |
| | | | | | | 15.99 (16.18, 15.67) |

FIG. 13

| Learning Goal | ASES | USA | Constant |
|---|---|---|---|
| | Follow-up | Follow-up | Follow-up |
| | Preop Composite ROM Score | Preop Composite ROM Score | Preop SPADI PROM |
| | Preop Active Abduction | Preop SPADI PROM | Preop Composite ROM Score |
| | Preop SPADI PROM | Preop Active Abduction | Preop Active Abduction |
| | Is surgery on dominant hand? | Preop Active External Rotation | Preop ASES PROM |

FIG. 14

| Feature Rank | Global Shoulder Elevation | VAS Pain | Abduction | External Rotation | External Rotation |
|---|---|---|---|---|---|
| 1 | Follow-up | Follow-up | Follow-up | Follow-up | Follow-up |
| 2 | Is surgery on dominant hand? | Is surgery on dominant hand? | Is surgery on dominant hand? | Is surgery on dominant hand? | Is surgery on dominant hand? |
| 3 | Preop Active Abduction | Is gender female? | Is gender female? | Is gender female? | Is gender female? |
| 4 | Preop Composite ROM Score | Preop Composite ROM Score | Did patient have previous shoulder surgery? | Preop SPADI PROM | Preop Active Abduction |
| 5 | Preop SPADI PROM | Preop SPADI PROM | Preop Active Abduction | Preop Active Abduction | Preop SPADI PROM |

FIG. 15

| Model Inputs | User Input or Calculation? | Pre-CT Planning Inputs | Planning Predictive | Post CT Model |
|---|---|---|---|---|
| Patient Age | User Input | Pre-CT Model | Planning | Predictive |
| Patient Gender | User Input | Pre-CT Model | Planning | Predictive |
| Patient Height | User Input | Pre-CT Model | Planning | Predictive |
| Patient Weight | User Input | Pre-CT Model | Planning | Predictive |
| Patient BMI | Calculation | Pre-CT Model | Planning | Predictive |
| Previous Shoulder Surgery? | User Input | Pre-CT Model | Planning | Predictive |
| Is shoulder surgery on dominant shoulder? | User Input | Pre-CT Model | Planning | Predictive |
| Indicate Patient Diagnoses | User Input | Pre-CT Model | Planning | Predictive |
| Indicate Patient Comorbidities | User Input | Pre-CT Model | Planning | Predictive |
| Preoperative Active Abduction ROM Measurement | User Input | Pre-CT Model | Planning | Predictive |
| Preoperative Active Forward Elevation ROM Measurement | User Input | Pre-CT Model | Planning | Predictive |
| Preoperative Active External Rotation ROM Measurement | User Input | Pre-CT Model | Planning | Predictive |
| Preoperative Passive External Rotation ROM Measurement | User Input | Pre-CT Model | Planning | Predictive |
| Preoperative Active IR Score ROM Measurement | User Input | Pre-CT Model | Planning | Predictive |
| Preoperative External Rotation Lag | Calculation | Pre-CT Model | Planning | Predictive |
| Preoperative Composite ROM Score | Calculation | Pre-CT Model | Planning | Predictive |

FIG. 20

| Preoperative Plan Choice (daily basis) | User Input | Pre-CT Model | Planning | Predictive |
|---|---|---|---|---|
| Preoperative Plan Using on Attachments | User Input | Pre-CT Model | Planning | Predictive |
| Preoperative Plan Tracking Lack of sleep | User Input | Pre-CT Model | Planning | Predictive |
| Preoperative Plan Tracking alcohol use | User Input | Pre-CT Model | Planning | Predictive |
| Preoperative Plan on Affinity | User Input | Pre-CT Model | Planning | Predictive |
| Preoperative Linking Smoking Handling Device | User Input | Pre-CT Model | Planning | Predictive |
| Preoperative Clinical Information | From GPS Planning Software | Post-CT Model | Planning | Predictive |
| Preoperative Clinical Past Med | From GPS Planning Software | Post-CT Model | Planning | Predictive |
| Preoperative Historical Information | From GPS Planning Software | Post-CT Model | Planning | Predictive |
| Stemed Implant Type (Cemented or Cementless CT Model) | From GPS Planning Software | Post-CT Model | Planning | Predictive |
| Cement Use | From GPS Planning Software | Post-CT Model | Planning | Predictive |
| Humeral Head Diameter | From GPS Planning Software | Post-CT Model | Planning | Predictive |
| Humeral Head Cut Thickness | From GPS Planning Software | Post-CT Model | Planning | Predictive |
| Glenosphere Size | From GPS Planning Software | Post-CT Model | Planning | Predictive |
| Glenosphere Diameter | From GPS Planning Software | Post-CT Model | Planning | Predictive |
| Glenosphere Type | From GPS Planning Software | Post-CT Model | Planning | Predictive |
| Lateral Mismatch | Calculation | Post-CT Model | Planning | Predictive |
| Humeral Stem Size | From GPS Planning Software | Post-CT Model | Planning | Predictive |
| Humeral Stem Type | From GPS Planning Software | Post-CT Model | Planning | Predictive |

FIG. 20 (CONTINUED)

| Model Inputs | User Input or Calculation? | Pre-CT planning or Post-CT planning Predictive Model input? | | |
|---|---|---|---|---|
| Ability to put on Coat? | User Input | Pre-CT Model | Planning | Predictive |
| Comfort of Sleep? | User Input | Pre-CT Model | Planning | Predictive |
| Wash Back/Fasten Bra? | User Input | Pre-CT Model | Planning | Predictive |
| Personal Hygiene and Toilet Needs? | User Input | Pre-CT Model | Planning | Predictive |
| Wash/Comb Hair? | User Input | Pre-CT Model | Planning | Predictive |
| Reach above head for an item? | User Input | Pre-CT Model | Planning | Predictive |
| Lift to the above head? | User Input | Pre-CT Model | Planning | Predictive |
| Throw a ball overhand? | User Input | Pre-CT Model | Planning | Predictive |
| Do usual work? | User Input | Pre-CT Model | Planning | Predictive |
| Do usual sport? | User Input | Pre-CT Model | Planning | Predictive |
| Pre-op ASES Score | Calculation | Pre-CT Model | Planning | Predictive |

Figure 25:
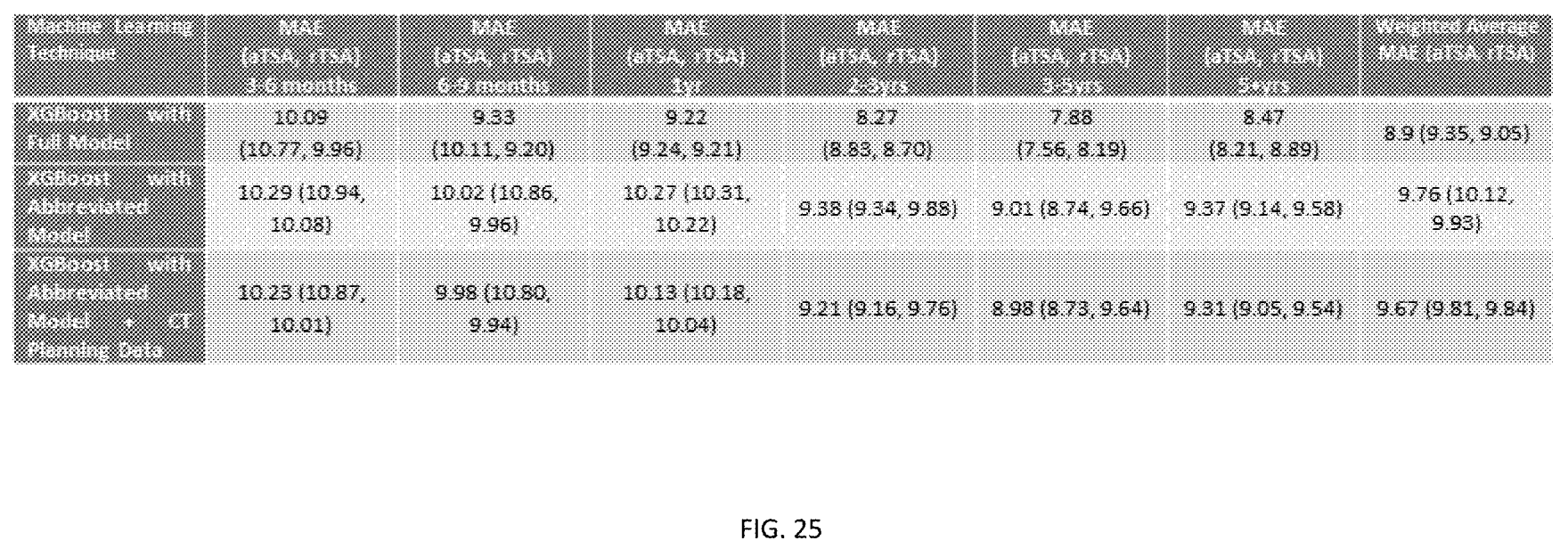

| | Day 1 | Day 2 | Day 3 | Day 4 | Day 5 | Day 6 |
|---|---|---|---|---|---|---|
| | 10.09 (10.77, 9.96) | 9.33 (10.11, 9.20) | 9.22 (9.24, 9.21) | 8.27 (8.83, 8.70) | 7.88 (7.56, 8.19) | 8.47 (8.21, 8.89) | 8.9 (9.35, 9.05) |
| | 10.29 (10.94, 10.08) | 10.02 (10.86, 9.96) | 10.27 (10.31, 10.22) | 9.36 (9.34, 9.88) | 9.01 (8.74, 9.66) | 9.37 (9.14, 9.58) | 9.76 (10.12, 9.93) |
| | 10.23 (10.87, 10.01) | 9.98 (10.80, 9.94) | 10.13 (10.18, 10.04) | 9.21 (9.16, 9.76) | 8.98 (8.73, 9.64) | 9.31 (9.05, 9.54) | 9.67 (9.81, 9.84) |

| | | | | | | |
|---|---|---|---|---|---|---|
| | 20.45 (20.50, 20.43) | 20.25 (20.39, 20.03) | 17.38 (17.93, 17.02) | 15.37 (14.95, 17.51) | 15.22 (15.17, 15.26) | 15.67 (16.14, 15.03) | 17.6 (18.03, 17.81) |
| | 21.92 (21.93, 21.91) | 21.88 (21.96, 21.44) | 18.96 (19.12, 18.65) | 17.82 (17.47, 18.92) | 16.92 (16.90, 16.95) | 16.21 (16.88, 16.09) | 19.22 (19.71, 19.24) |
| | 21.83 (21.84, 21.80) | 21.84 (21.90, 21.39) | 18.91 (19.09, 18.60) | 17.01 (16.86, 17.83) | 16.90 (16.89, 16.91) | 16.20 (16.88, 16.08) | 19.04 (19.22, 19.12) |

FIG. 29

| Model prediction | Asystole (TSE) | Extreme (TSE) | Global Ischemia Partial (TSE) | Fast (TSE) | Abnormal (TSE) | Partial Ischemia (TSE) | Extreme Ischemia (TSE) |
|---|---|---|---|---|---|---|---|
|  | 13.6 (17.0, 10.3) | 5.7 (12.8, -0.3) | 1.4 (1.7, 1.0) | 1.6 (2.7, 1.4) | 7.0 (13.9, 1.9) | 12.0 (23.1, -2.9) | 3.0 (14.5, -5.3) |
| Precision | 77.9% (72.9%, 80.6%) | 71.3% (63.0%, 77.6%) | 75.7% (75.5%, 75.8%) | 75.3% (66.5%, 77.9%) | 83.5% (78.2%, 88.7%) | 73.9% (73.4%, 92.7%) | 84.7% (77.8%, 90.4%) |
| Recall | 95% (94%, 95%) | 96% (97%, 98%) | 94% (96%, 93%) | 92% (91%, 91%) | 94% (91%, 98%) | 92% (87%, 99%) | 95% (90%, 99%) |
| F1 | 99% (97%, 99%) | 99% (99%, 100%) | 96% (95%, 98%) | 98% (97%, 99%) | 94% (91%, 98%) | 95% (88%, 99%) | 96% (93%, 99%) |
| Accuracy | 95% (94%, 95%) | 97% (96%, 99%) | 92% (93%, 92%) | 93% (82%, 91%) | 90% (86%, 98%) | 89% (82%, 99%) | 95% (92%, 99%) |
| AUC | 0.90 (0.90, 0.88) | 0.95 (0.97, 0.96) | 0.88 (0.91, 0.87) | 0.87 (0.89, 0.82) | 0.83 (0.80, 0.98) | 0.79 (0.75, 0.95) | 0.83 (0.73, 0.95) |

FIG. 31

| | AIS (TSA) [%] | Cerebellum TSA [%] | Cerebellum Brainstem (TSA) [%] | Vastpath (TSA) [%] | Diabetic (TSA) [%] | External cerebellum [%] | External metastasis [%] |
|---|---|---|---|---|---|---|---|
| Patient count (%) | 31.5 (37.6, 25.9) | 19.1 (25.4, 13.6) | 3.1 (3.9, 2.4) | 3.2 (3.8, 2.6) | 28.5 (36.1, 19.6) | 35.4 (45.5, 22.3) | 11.7 (20.1, 3.6) |
| Prevalence | 66.7% (57.3%, 52.8%) | 62.3% (52.8%, 70.7%) | 58.8% (57.4%, 61.5%) | 62.8% (61.5%, 55.2%) | 64.7% (55.2%, 48.4%) | 61.3% (48.4%, 64.6%) | 70.1% (64.6%) |
| | 73.1% | 71.7% | 70.7% | 72.5% | 73.9% | 75.7% | 82.0% |
| Precision | 88% (89%, 88%) | 91% (93%, 94%) | 89% (91%, 91%) | 85% (92%, 88%) | 86% (80%, 89%) | 85% (85%, 91%) | 85% (79%, 92%) |
| Recall | 93% (93%, 94%) | 95% (88%, 97%) | 93% (86%, 90%) | 99% (92%, 97%) | 86% (87%, 87%) | 91% (88%, 93%) | 89% (92%, 93%) |
| Accuracy | 87% (89%, 88%) | 91% (90%, 92%) | 85% (87%, 86%) | 86% (89%, 88%) | 82% (81%, 83%) | 84% (86%, 88%) | 81% (79%, 88%) |
| AUC | 0.84 (0.89, 0.81) | 0.90 (0.90, 0.88) | 0.84 (0.87, 0.84) | 0.82 (0.86, 0.81) | 0.81 (0.80, 0.78) | 0.83 (0.87, 0.83) | 0.76 (0.74, 0.78) |

FIG. 33

| Segmentation with fine-tuned model trained on | Aorta (TSA) | Content (EUSA/TSA) | Global Shoulder Function (EUSA/TSA) | Vaspra (EUSA/TSA) | Abduction (EUSA/TSA) | Forward Elevation (EUSA/TSA) | External rotation (TSA) |
|---|---|---|---|---|---|---|---|
| Precision | 88% (88%, 86%) | 90% (91%, 92%) | 82% (89%, 91%) | 85% (92%, 86%) | 82% (76%, 83%) | 78% (74%, 86%) | 82% (76%, 89%) |
| Recall | 92% (92%, 93%) | 94% (84%, 96%) | 93% (86%, 90%) | 99% (92%, 97%) | 83% (83%, 83%) | 88% (81%, 91%) | 88% (89%, 91%) |
| Accuracy | 87% (89%, 88%) | 90% (88%, 90%) | 84% (85%, 86%) | 86% (89%, 88%) | 80% (79%, 81%) | 82% (82%, 86%) | 78% (76%, 84%) |
| AUC | 0.83 (0.86, 0.77) | 0.89 (0.89, 0.87) | 0.83 (0.86, 0.83) | 0.83 (0.85, 0.82) | 0.72 (0.73, 0.71) | 0.74 (0.78, 0.71) | 0.74 (0.71, 0.76) |

FIG. 36

METHOD AND SYSTEM FOR MODELING PREDICTIVE OUTCOMES OF ARTHROPLASTY SURGICAL PROCEDURES

CROSS-REFERENCE TO RELATED APPLICATION

This application is a Section 111(a) application relating to and claiming the benefit of commonly owned, U.S. Provisional Patent Application No. 63/011,871, titled "MACHINE LEARNING TECHNIQUES TO PREDICT CLINICAL OUTCOMES AFTER SHOULDER ARTHROPLASTY," having a filing date of Apr. 17, 2020, the contents of which are incorporated by reference herein in their entirety.

FIELD

The present disclosure relates to machine learning modeling for medical applications, and more specifically to method and system for modeling predictive outcomes of arthroplasty surgical procedures.

BACKGROUND

Supervised machine learning is a class of artificial intelligence by which the computer learns the complex structure and relationships in large datasets to create predictive models with the help of labeled features. The machine learning model iteratively learns using the feature data to minimize predictive error. There are numerous commercial applications of various machine learning techniques.

SUMMARY

In some embodiments, the present disclosure provides an exemplary technically improved computer-based apparatus that includes at least the following components of a processor and a non-transitory memory storing instructions which, when executed by the processor, cause the processor to receive pre-operative patient specific data for an arthroplasty surgery to be performed on a joint of a patient, where the pre-operative patient specific data may include a medical history of the patient, a measured range of movement for at least one type of joint movement of the joint, and at least one pain metric associated with the joint, to input the pre-operative patient specific data to at least one first machine learning model to determine a first predicted post-operative joint performance data output, where the first predicted post-operative joint performance data output may include at least one first predicted post-operative outcome metric of the joint, to display the first predicted post-operative joint performance data output on a display to a user, to receive at least one medical image of the joint obtained from at least one medical imaging procedure performed on the patient, to generate a reconstruction plan of the joint of the patient based on the at least one medical image of the joint, and at least one arthroplasty surgical parameter obtained from the user in response to the displayed first predicted post-operative joint performance data output, where the reconstruction plan may include the at least one arthroplasty surgical parameter that is selected from at least one implant, at least one implant size, at least one arthroplasty surgical procedure, at least one position for implanting the at least one implant in the joint, or any combination thereof, to input the at least one arthroplasty surgical parameter into at least one second machine learning model to determine a second predicted post-operative joint performance data output including at least one second predicted post-operative outcome metric of the joint, to display the second predicted post-operative joint performance data output on the display to the user, and to update the displayed second predicted post-operative joint performance data output to include at least one arthroplasty surgery recommendation, in response to the user varying any of the at least one arthroplasty surgical parameter before the arthroplasty surgery, during the arthroplasty surgery, or both.

In some embodiments, the present disclosure provides an exemplary technically improved computer-based method that includes at least the following steps of receiving, by a processor, pre-operative patient specific data for an arthroplasty surgery to be performed on a joint of a patient. The pre-operative patient specific data may include a medical history of the patient, a measured range of movement for at least one type of joint movement of the joint, and at least one pain metric associated with the joint. The pre-operative patient specific data may be inputted by the processor to at least one first machine learning model to determine a first predicted post-operative joint performance data output. The first predicted post-operative joint performance data output may include at least one first predicted post-operative outcome metric of the joint. The first predicted post-operative joint performance data output may be displayed by the processor on a display to a user. At least one medical image of the joint obtained from at least one medical imaging procedure performed on the patient may be received by the processor. A reconstruction plan of the joint of the patient may be generated by the processor based on the at least one medical image of the joint, and at least one arthroplasty surgical parameter obtained from the user in response to the displayed first predicted post-operative joint performance data output. The reconstruction plan may include the at least one arthroplasty surgical parameter that is selected from at least one implant, at least one implant size, at least one arthroplasty surgical procedure, at least one position for implanting the at least one implant in the joint, or any combination thereof. The at least one arthroplasty surgical parameter may be inputted by the processor into at least one second machine learning model to determine a second predicted post-operative joint performance data output comprising at least one second predicted post-operative outcome metric of the joint. The second predicted post-operative joint performance data output may be display by the processor on the display to the user. The displayed second predicted post-operative joint performance data output may be updated by the processor to include at least one arthroplasty surgery recommendation, in response to the user varying any of the at least one arthroplasty surgical parameter before the arthroplasty surgery, during the arthroplasty surgery, or both.

DRAWINGS

Some embodiments of the disclosure are herein described, by way of example only, with reference to the accompanying drawings. With specific reference now to the drawings in detail, it is stressed that the embodiments shown are by way of example and for purposes of illustrative discussion of embodiments of the disclosure. In this regard, the description taken with the drawings makes apparent to those skilled in the art how embodiments of the disclosure may be practiced.

FIG. 5 is a table showing minimally clinically important difference (MCID) and substantial clinical benefit (SCB) thresholds for each outcome metric for the overall cohort, aTSA, and rTSA, in accordance with one or more embodiments of the present disclosure;

FIG. 7 is a table showing a comparison of Mean Absolute Error (MAE) associated with University of California, Los Angeles (UCLA) Prediction Models in accordance with one or more embodiments of the present disclosure;

FIG. 8 is a table showing a comparison of Mean Absolute Error (MAE) associated with Constant Prediction Models in accordance with one or more embodiments of the present disclosure;

FIG. 9 is a table showing a comparison of Mean Absolute Error (MAE) associated with Global Shoulder Function Score Prediction Models in accordance with one or more embodiments of the present disclosure;

FIG. 10 is a table showing a comparison of Mean Absolute Error (MAE) associated with visual analogue scale (VAS) Pain Score Prediction Models in accordance with one or more embodiments of the present disclosure;

FIG. 12 is a table showing a comparison of Mean Absolute Error (MAE) associated with Active Forward Elevation Prediction Models in accordance with one or more embodiments of the present disclosure;

FIG. 13 is a table showing a comparison of Mean Absolute Error (MAE) associated with Active External Rotation Prediction Models in accordance with one or more embodiments of the present disclosure;

FIG. 14 is a table showing a comparison of the top five most-predictive features as identified by an XGBoost machine learning algorithm to predict patient reported outcome measures (PROM) as ranked by F-score in accordance with one or more embodiments of the present disclosure;

FIG. 15 is a table showing a comparison of the five most-predictive features as identified by an XGBoost machine learning algorithm to predict pain, function, and ROM as ranked by F-score in accordance with one or more embodiments of the present disclosure;

FIG. 20 is a table showing a list of predictive model inputs to machine learning models for calculating the Global Shoulder Function Score, the VAS Pain Score, and Active Abduction, Active Forward Elevation, and Active External Rotation in accordance with one or more embodiments of the present disclosure;

FIG. 21 is a table showing a list of additional predictive model inputs (over the inputs presented in FIG. 20) to machine learning models for calculating an ASES score in accordance with one or more embodiments of the present disclosure;

FIG. 22 is a table showing a list of additional predictive model inputs (over the inputs presented in FIG. 20) to machine learning models for calculating a Constant Score in accordance with one or more embodiments of the present disclosure;

FIG. 24 is a table showing a comparison of Mean Absolute Error (MAE) associated with the ASES predictions using the Full and Abbreviated XGBoost machine learning models in accordance with one or more embodiments of the present disclosure;

FIG. 25 is a table showing a comparison of Mean Absolute Error (MAE) associated with the constant predictions using the Full and Abbreviated XGBoost machine learning models in accordance with one or more embodiments of the present disclosure;

FIG. 27 is a table showing a comparison of Mean Absolute Error (MAE) associated with the VAS Pain Score Predictions using the Full and Abbreviated XGBoost machine learning models in accordance with one or more embodiments of the present disclosure;

FIG. 28 is a table showing a comparison of Mean Absolute Error (MAE) associated with the Active Abduction Predictions using the Full and Abbreviated XGBoost machine learning models in accordance with one or more embodiments of the present disclosure;

FIG. 29 is a table showing a comparison of Mean Absolute Error (MAE) associated with the Active Forward Elevation Predictions using the Full and Abbreviated XGBoost machine learning models in accordance with one or more embodiments of the present disclosure;

FIG. 31 is a table showing a comparison of a full XGBoost model predictions for aTSA and rTSA patients that experienced a clinical improvement exceeding the MCID threshold for multiple different outcome measures in accordance with one or more embodiments of the present disclosure;

FIG. 33 is a table showing a comparison of a full XGBoost model predictions for aTSA and rTSA patients that experienced a clinical improvement exceeding the SCB threshold for multiple different outcome measures in accordance with one or more embodiments of the present disclosure;

Figure 37:
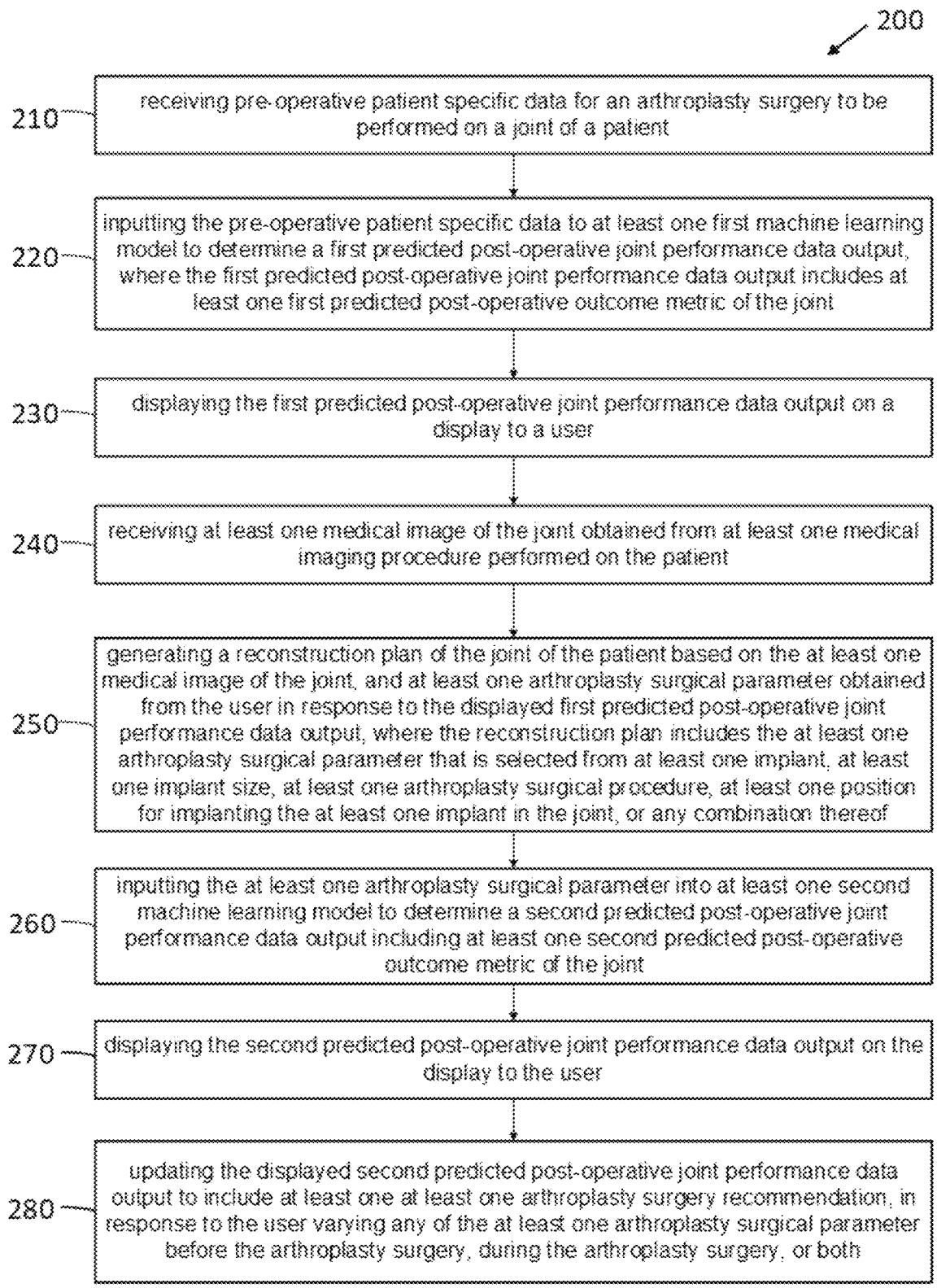

FIG. 36 is a table showing a comparison of an abbreviated XGBoost model with inputs from CT planning data to make predictions for aTSA and rTSA patients that experienced a clinical improvement exceeding the SCB threshold for multiple different outcome measures in accordance with one or more embodiments of the present disclosure; and FIG. 37 is a flowchart of an exemplary method for modeling predictive outcomes of arthroplasty surgical procedures in accordance with one or more embodiments of the present disclosure.

DETAILED DESCRIPTION

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, terms such as "comprising" "including," and "having" do not limit the scope of a specific claim to the materials or steps recited by the claim.

All prior patents, publications, and test methods referenced herein are incorporated by reference in their entireties.

Examples

Variations, modifications and alterations to embodiments of the present disclosure described above will make themselves apparent to those skilled in the art. All such variations, modifications, alterations and the like are intended to fall within the spirit and scope of the present disclosure, limited solely by the appended claims.

While several embodiments of the present disclosure have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

Any feature or element that is positively identified in this description may also be specifically excluded as a feature or element of an embodiment of the present as defined in the claims.

Machine learning techniques for healthcare applications offer the potential to transform complex healthcare data into practical knowledge that can help surgeons better understand their patients and the complexities of their patient's conditions. By leveraging large quantities of high-quality clinical outcomes data, machine learning analyses can identify previously hidden correlations and relationships in datasets to create predictive models that can better inform individual patient treatment decisions.

In orthopedics, predictive models derived from high-quality outcomes and patient data may represent a patient-specific implementation of evidence-based decision-making tools, that may transform complex healthcare data into practical knowledge to support more-informed treatment decision making. While the commercial usage of machine learning may be new to orthopedics, its usage in research has increased in recent years. Many machine learning applications have been image-based analyses, but there is a growing interest to use machine learning techniques to predict clinical outcomes. Predictive outcomes models may assist the orthopedic surgeon to better identify which patients will benefit from elective procedures, such as arthroplasty, and also help better-align patient and surgeon expectations for clinical improvement by leveraging the experiences of previous patients with similar demographics, diagnoses, comorbidities, clinical history, and treatments. With more insight into the factors that predict patient-specific improvement, and with better alignment between predicted and actualized outcomes, patient satisfaction levels may likely increase through the use of such an evidenced-based predictive outcomes tool.

Embodiments of the present disclosure herein describe methods and systems for modeling predictive outcomes of arthroplasty surgical procedures. Arthroplasty may be used to repair or replace any joint in the body, including but not limited to the hips, knees, shoulders, elbows, and ankles, for example. However, to further illustrate these methods and systems, shoulder arthroplasty is used herein as an exemplary embodiment throughout this disclosure.

Figure 1:
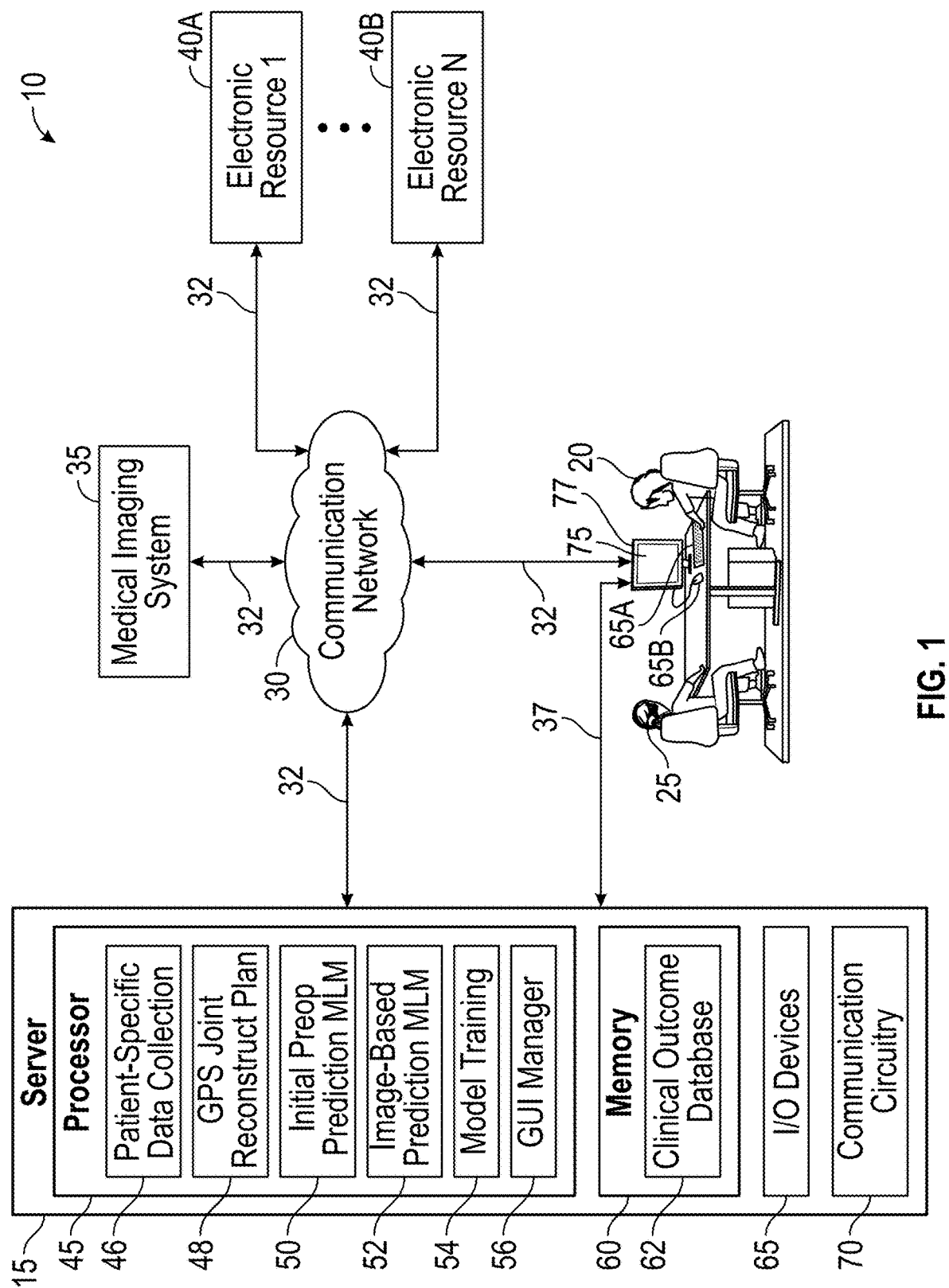
FIG. 1 is a block diagram of a system for modeling predictive outcomes of arthroplasty surgical procedures in accordance with one or more embodiments of the present disclosure.

FIG. 1 is a block diagram of a system 10 for modeling predictive outcomes of arthroplasty surgical procedures in accordance with one or more embodiments of the present disclosure. The system 10 may include a server 15, a medical imaging system 35, a plurality of N electronic medical resources denoted ELECTRONIC RESOURCE1 40A . . . ELECTRONIC RESOURCEN 40B, where N is an integer, and a computing device 77 of a user 20 all communicating 32 over a communication network 30. The computing device 77 of the user 20 may also be communicatively coupled 37 directly to the server 15.

In some embodiments, the user 20, that may interact with a graphic user interface (GUI) 75 on the computing device 77, may be a physician discussing an arthroplasty surgical procedure to be performed on a patient 25. In other embodiments, the computing device 77 may be placed in any suitable location such as an operating room where the joint arthroplasty surgical procedure may be performed.

The server 15 may include a processor 45, a non-transitory memory 60, a communication circuitry 70 for communicating 32 over the communication network 30, and/or I/O devices 65, such as a display for displaying the GUI 75 to the user 20, a keyboard 65A and a mouse 65B, for example.

In some embodiments, the server 15 may be configured to execute different software modules to perform the functions in the system 10 as described herein. The different software modules may include, but are not limited to, a patient-specific data collection module 46, a computed tomography (CT) image-based guided personalized surgery (GPS) Joint Reconstruction Planning module 48, an initial pre-op prediction machine learning model (MLM) module 50, an image-based Prediction MLM module 52, a machine learning model training module 54, and a GUI manager module 56 for controlling the GUI 75 on the user's computing device 77.

In some embodiments, the non-transitory memory 60 may be configured to store a clinical outcome database 62 with a plurality of clinical outcomes of different types of arthroplasty surgical procedures performed on a plurality of patients.

In some embodiments, the patient-specific data collection module 46 may query any of the plurality of electronic medical resources 40A and 40B over the communication network 30 to obtain medical data from the patient 25. The plurality of electronic medical resources 40A and 40B may be managed by the patient's health management organization HMO, a hospital that the patient 25 received medical treatment, a doctor that the patient 25 received medical treatment, for example.

In some embodiments, the CT image-based GPS Joint Reconstruction Plan module 48 may analyze the data from medical images received from the medical imaging system 35. The medical imaging system 35 may generate an X-ray image, a computed tomography (CT) image, a magnetic resonance image, and/or a three-dimensional (3D) medical image, for example. The 3D medical image may be generated from a plurality of X-ray images. The medical image may include a frame from a video of the joint.

In some embodiments, the machine learning model (MLM) training module 54 may generate a training dataset for training the machine learning models used in the system 10. For example, MLM training module 54 may retrieve patient outcome data from the clinical outcome database 62 to generate a dataset that maps, in part, data vectors of pre-operative patient specific data and arthroplasty surgical parameters used in different types of arthroplasty surgical procedures to known post-operative outcome metrics of the joint replacement. The trained machine learning models may then generate predicted post-operative outcome metrics of the joint replacement given the input data vectors for a new patient prior to arthroplasty surgery.

In some embodiments, with regard to shoulder arthroplasty, machine learning techniques may be used to pre-operatively predict clinical outcomes at various post-operative timepoints after surgery for patients receiving total shoulder arthroplasty. These predictions may be used to inform the shoulder surgeon of what a particular patient may expect to experience after anatomic total shoulder arthroplasty (aTSA) and/or reverse total shoulder arthroplasty (rTSA), for example. A list of model inputs may be obtained from the health care professional and/or automatically from the patient's electronic medical record through software integration by querying any of the electronic medical resources as previously described. While this disclosure focuses on aTSA and rTSA outcomes prediction, these models could also be applied to other shoulder arthroplasty applications, like hemiarthroplasty, fracture reconstruction, endoprostheses, resurfacing, and primary vs. revision arthroplasty outcomes predictions.

In some embodiments, regarding the inputs to these predictive models, the predictive outcomes for a given total shoulder arthroplasty patient may be further refined to provide recommendations for optimal clinical outcomes using different implant sizes, such as different sizes of humeral heads, humeral stems, glenospheres, glenoid or humeral augments, for example, implant types, such as aTSA, rTSA, hemiarthroplasty, resurfacing, short stem, stemless, fracture arthroplasty, endoprostheses, revision devices, for example, and/or surgical techniques, such as delto-pectoral, superior-lateral, subscapularis sparing, for example, in order to account for the patient specific diagnoses and bone/soft tissue morphological considerations.

In some embodiments, using machine learning predictive outcome algorithms to pre-operatively predict a patient's post-operative clinical outcomes may have numerous additional practical applications that are valuable to the patient and surgeon. First, the ability to differentiate pre-operatively which patients may achieve clinical improvement after aTSA and rTSA relative to patient satisfaction anchor-based minimal clinically important difference (MCID) and substantial clinical benefit (SCB) thresholds for multiple different patient reported outcome measures (PROMs) and active range of motion (ROM) measurements may be useful to the orthopedic surgeon to objectively identify which patients are appropriate candidates for these elective procedures. It may also assist the orthopedic surgeon to decide between implant types for a particular patient. As a non-operative treatment may be best for some patients, this foreknowledge may represent a more efficient resource allocation for the patient, surgeon, hospital, and/or payer.

In this disclosure, the terms "outcome metric" and "outcome measure" may be used interchangeably herein. The terms "machine learning model", "machine learning module", "machine learning predictive outcome algorithms", "predictive outcome algorithms" and/or "predictive outcome model" may be used interchangeably herein.

In some embodiments, a patient-specific prediction of clinical improvement at multiple post-surgical timepoints may be helpful to align patient and surgeon expectations on what is achievable after this elective procedure. Given the association between pre-operative expectations and post-operative satisfaction, better surgeon-patient alignment on both the magnitude and rate of clinical improvement may result in greater levels of patient satisfaction. Furthermore, an improved understanding of the amount of clinical improvement that can be expected at different post-surgical timepoints for a given patient may aid the surgeon in establishing protocols for rehabilitation. This may also help both the surgeon and patient weigh these gains versus the procedure-specific risks associated with aTSA and rTSA, such as: instability, aseptic loosening, and infection.

In some embodiments, the machine learning techniques disclosed herein may be extended to predict outcomes and improvement based upon specific diagnoses and to also predict and/or identify patients with risk factors for various complications. Furthermore, the predictive models may help appropriately risk-stratify patients and make recommendations on healthcare workflows, such as identifying patients that may safely have surgery in an ambulatory surgical center or patients that should have an in-patient vs. outpatient surgery in a hospital. The predictive models may make recommendations for a specific patient on their duration length for hospital stay after the arthroplasty procedure.

In some embodiments, the predictive models may provide a better understanding of the factors influencing outcomes, which may assist the orthopedic surgeon to personalize care for each patient in terms of patient-specific requirements for pain relief, function, and mobility, as well as to help the patient better understand how well the arthroplasty surgical procedure may meet their needs based upon that patients unique characteristics that are input to and accounted for in the predictive model output.

Figure 2:
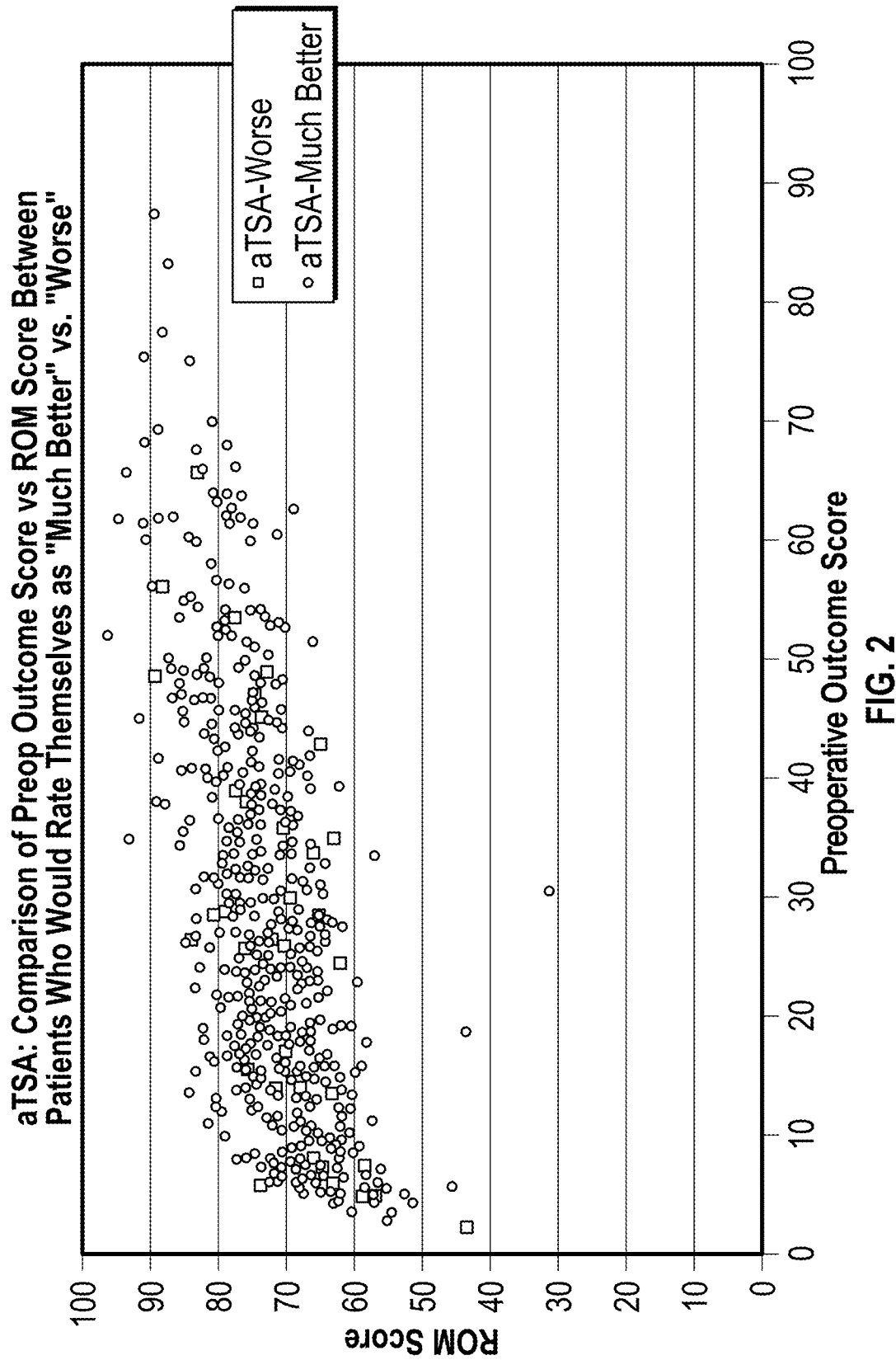
FIG. 2 is a graph illustrating a preoperative range of motion (ROM) score versus preoperative outcome scores comparing preoperative outcomes of anatomic total shoulder arthroplasty (aTSA) patients in a clinical outcome database who would later after their procedure go on to describe themselves as "Much Better" or "Worse" in accordance with one or more embodiments of the present disclosure.

FIG. 2 is a graph illustrating a preoperative range of motion (ROM) score versus preoperative outcome scores comparing preoperative outcomes of anatomic total shoulder arthroplasty (aTSA) patients in a clinical outcome database who would later after their procedure go on to describe themselves as "Much Better" or "Worse" in accordance with one or more embodiments of the present disclosure.

Figure 3:
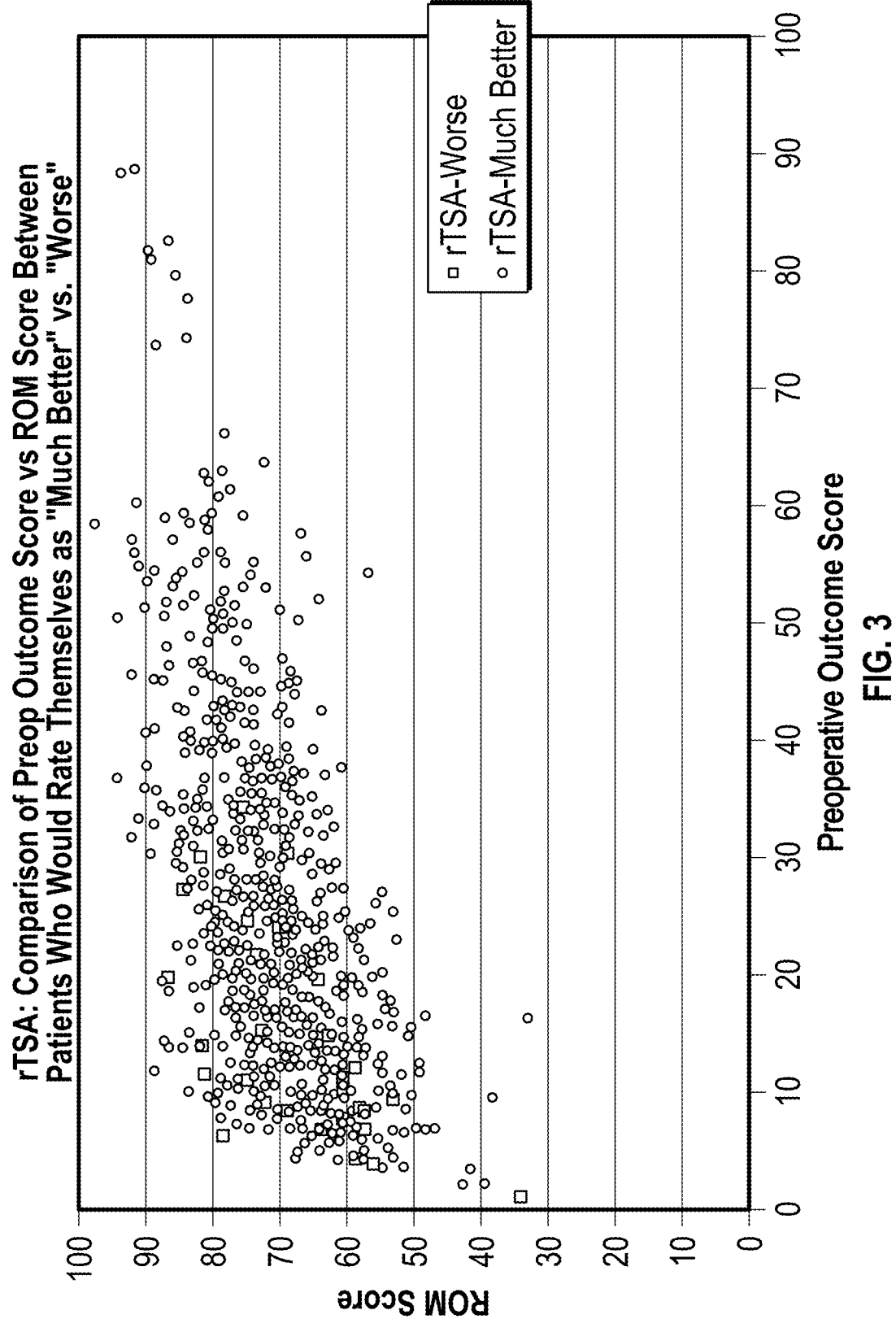
FIG. 3 is a graph illustrating a preoperative range of motion (ROM) score versus a preoperative outcome score comparing preoperative outcomes of reverse total shoulder arthroplasty (aTSA) patients in a clinical outcome database who would later after their procedure go on to describe themselves as "Much Better" or "Worse" in accordance with one or more embodiments of the present disclosure.

FIG. 3 is a graph illustrating a preoperative range of motion (ROM) score versus a preoperative outcome score comparing preoperative outcomes of reverse total shoulder arthroplasty (aTSA) patients in a clinical outcome database who would later after their procedure go on to describe themselves as "Much Better" or "Worse" in accordance with one or more embodiments of the present disclosure;

Note that in both FIGS. 2 and 3, the preoperative outcomes of aTSA and rTSA patients in the clinical outcome database 62 may be based on aTSA and rTSA patients that post-operatively rate themselves as "much better" versus those who rate themselves as "worse" during the latest post-operative follow-up. Note the relative equal distribution of patients between the two cohorts in both FIGS. 2 and 3 indicates that these patients may be difficult to identify by the orthopedic surgeon and distinguish based upon these parameters alone prior to surgery if a particular patient would have a "much better" or "worse" outcome, if the patient were to have a given procedure.

In some embodiments, evidence-based pre-operative predictive outcomes tool greatly assist surgeons objectively to establish patient-specific gains that will be achieved after arthroplasty because it is typically difficult for arthroplasty surgeons to pre-operatively identify as to which patients will achieve poor outcomes and which patients will be dissatisfied with the procedure based upon the currently available knowledge and clinical guidelines, and known risk factors.

Positive outcomes may be common for patients after total shoulder arthroplasty with about 90% of patients reporting that they are satisfied with their procedure (e.g., patients stating they are "better" or "much better" relative to their non-operative condition) for patients receiving aTSA and/or rTSA, as compared to patients who are unsatisfied (e.g., patients stating they are "unchanged" or "worse" relative to their non-operative condition). However, the predictability of patients who will achieve these poor outcomes may be less certain for both aTSA (FIG. 2) and rTSA (FIG. 3) as demonstrated by the presentation of preoperative outcomes as compared to patients who would go on to be "much better" as compared to those who would go on to be "worse" post-operatively.

Predictability of outcomes after total shoulder arthroplasty may be less certain when considering improvements in function and the amount of range of motion the patient will achieve in a given plane at a particular time of follow-up after surgery. For example, most shoulder surgeons may consider that improvement of active rotation and the amount of active rotation after rTSA is unpredictable so that they may not accurately advise patients if they will improve their ability to actively rotate their arm or not.

With regard to the recovery time for a patient to regain a full range of motion after total shoulder arthroplasty as well as full outcomes as measured by various patient reported outcome measures for measuring (PROMs: e.g. ASES, Constant, UCLA, Shoulder Function, Simple Shoulder Test (SST), Shoulder Pain And Disability Index (SPADI), VAS Pain, Shoulder Arthroplasty Smart Score, etc), the majority of improvement that a patient may experience is typically achieved within the first 6 months after the arthroplasty procedure. However, some patients may take as long as 2 years after the procedure to achieve the full range of motion or to obtain a maximum PROM score.

Additionally, the full range of motion and/or maximum PROM score may vary between patients, due to many different factors, including, for example, but not limited to patient demographics, comorbidities, diagnosis, severity of diagnosis/degenerative condition, bone/soft tissue quality, bone morphology, implant selection type, implant sizing, implant positioning, and/or surgical technique information. Thus, surgeon and patient expectations may not be accurate and may fail to align due to all of these above-mentioned factors, that may lead to increased dissatisfaction with the procedure. Thus, there exists a need to better and more accurately predict outcomes as defined by PROMs and ROM after total shoulder arthroplasty, taking into account all possible variables in order to better help patients and surgeons achieve more accurate expectations, improved predictability, and improved satisfaction.

Figure 4:
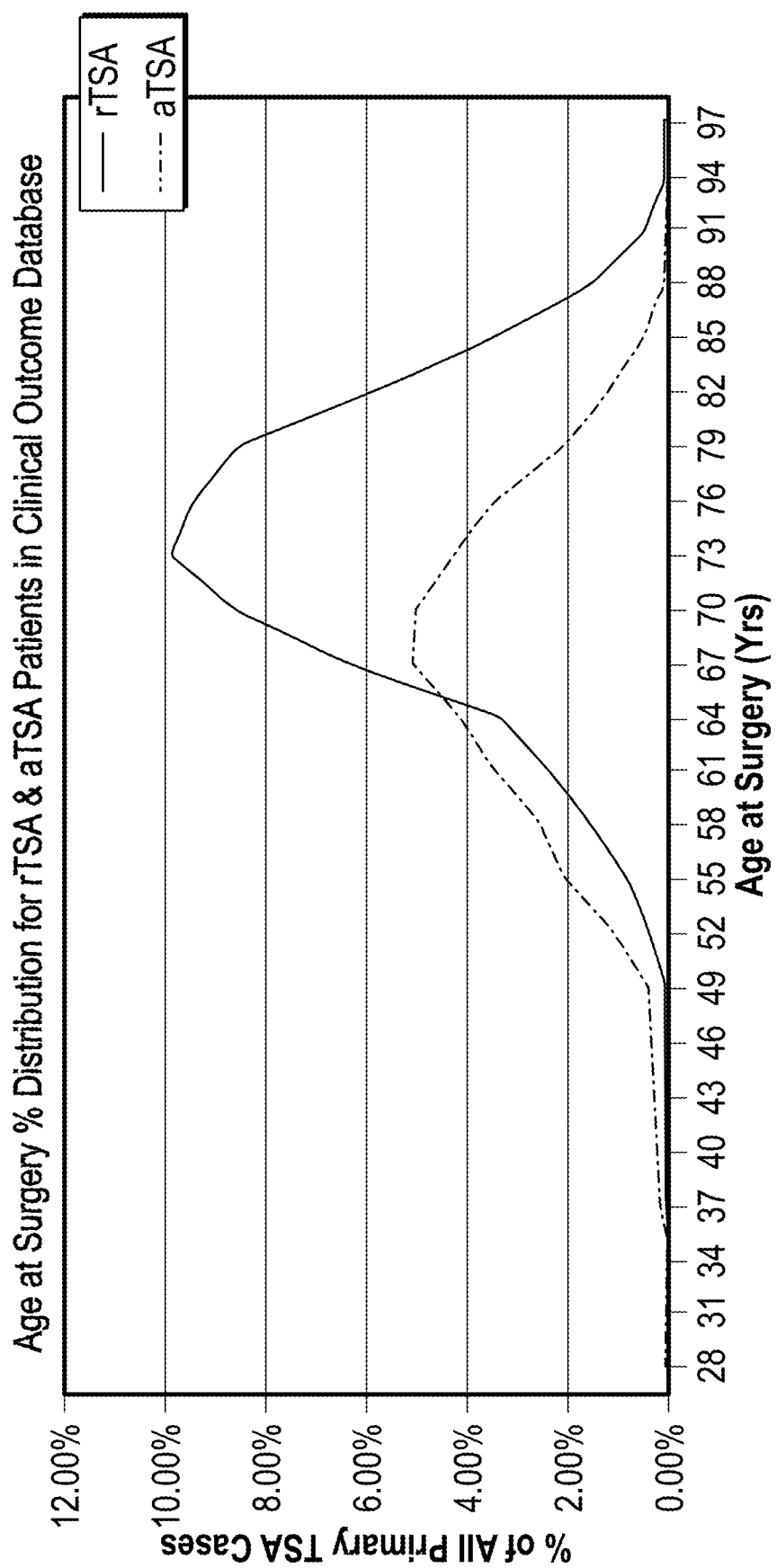
FIG. 4 is a graph illustrating an age at surgery distribution for anatomic total shoulder arthroplasty (aTSA) patients and reverse total shoulder arthroplasty (rTSA) in accordance with one or more embodiments of the present disclosure.

FIG. 4 is a graph illustrating an age at surgery distribution for anatomic total shoulder arthroplasty (aTSA) patients and reverse total shoulder arthroplasty (rTSA) in accordance with one or more embodiments of the present disclosure. FIG. 4 illustrates that older patients may be more likely to receive a rTSA procedure than an aTSA procedure, while younger patients may be more likely to received aTSA. The cross-over age by which patients are more likely to receive a rTSA is 64 years of age at the time of surgery. For patients older than 75 years of age at the time of surgery, the ratio is 4:1 for rTSA as compared to aTSA.

Additionally, due to a recent blending of indications between aTSA and rTSA, and also a recent shift in trends by shoulder surgeons to increase their usage of rTSA for older patients to mitigate the occurrences of rotator cuff related complications, which predominately occur with aTSA, and not rTSA, as shown in FIG. 4, there is a need to help surgeons better predict which arthroplasty procedure would provide better outcomes.

The embodiments herein describe a method, workflow, and computer software system as shown in the system 10 of FIG. 1 that predicts outcomes and range of motion of joints having underwent after arthroplasty surgical procedures using a multivariable-based machine learning analysis of outcomes data from the clinical outcome database 62 (e.g., that may be used for training the machine learning predictive model implemented herein). Thus, the trained machine learning predictive models may extrapolate those statistical trends and relationships to that of patient-specific data for a particular patient who would receive joint arthroplasty in order to more accurately predict prior to surgery, the post-operative outcome measures that particular patient may achieve.

In some embodiments, the surgeon may utilize this predictive model derived information to help identify outcomes as measured by multiple different outcome metrics at various post-surgical timepoints for various implant types and sizes and to also compare those predicted results to other similar patients from the clinical outcome database 62 so as to extrapolate their outcomes based upon the experiences of other similar patients.

In some embodiments, the predictive models may be used to compare range of outcomes achieved with different implant types (such as aTSA vs. rTSA for shoulder arthroplasty), different implant sizes, and different implant positions as compared to other patients in the clinical outcome database 62 for various defined diagnoses, comorbidities, bone deformities, and/or soft-tissue conditions within the joint under consideration. All of these considerations may be used to establish and communicate more accurate expectations of actual results, and better surgeon-to-patient alignment.

In some embodiments, the predictive model may utilize data from the clinical outcome database 62 to identify the complex interactions in this data, classify the data, and/or identify the most important contributors and associations to post-operative outcomes. These predictive algorithms may further model and predict post-operative results for similar new cases for various different PROMs and range of motion measures. Each of the predictive models may be analyzed alone and/or concatenated in a series where the results of one predictive model may be an input to another new predictive model.

In some embodiments, the predictive models for total shoulder arthroplasty generated in for the exemplary embodiments shown in this disclosure were trained using data from the clinical outcome database 62 from more than 8,000 patients and 20,000 post-operative patient visits. There were about 300 pre-operative data inputs for each patient on which to base the analysis. This predictive analysis may perform a regression analysis, a deep-learning based analysis, at least one ensemble-based decision tree learning method, or any combination thereof, so as to combine outcomes from multiple various decision trees to identify and rank the pre-operative parameters that most significantly relate to outcomes with total shoulder arthroplasty.

In some embodiments, by identifying and ranking these parameters as well as the most-relevant risk factors out of data related to patient demographics, comorbidities, diagnosis, severity of diagnosis/degenerative condition, bone/soft tissue quality, bone morphology, implant selection type, implant sizing, implant positioning, and/or surgical technique information, for example, the predictive models may aid the surgeon to provide the best outcomes possible for a particular patient by leveraging this large database of clinical history. The predictive models may provide actionable recommendations to the surgeon in identifying and communicating these complex interactions between these parameters.

In some embodiments, the system 10 by which the predictive models may be accessed on the computing device 77 by the surgeon 20 may be a pre-operative planning software, that provides recommendations on which implant types and implant sizes that the surgeon may select and provide recommendations for where these implants should be positioned.

In some embodiments, the system 10 by which the predictive models may be accessed on the computing device 77 by the surgeon 20 may provide a GUI 75 for an intra-operative computer navigation or robotic system which permits on the fly changes to the pre-operative plan based upon intra-operative findings by the surgeon and/or hospital staff (e.g., during the surgical procedure). Each of the aforementioned actionable guidance may be communicated by the predictive models intra-operatively (e.g. implant type, implant size, and/or implant position). Conversely, the predictive model may be accessed via a stand-alone software application available on multiple different software platforms which may be accessible to the patient, surgeon, or other healthcare professional.

In some embodiments, three supervised machine learning techniques may be used including a linear-regression-based, a tree-based, and/or a deep-learning-based machine learning, to analyze data on the clinical outcome database 62 of shoulder arthroplasty patients who received a single platform shoulder prosthesis (see, for example, Equinoxe, Exactech Inc., Gainesville, Fla.) between November 2004 and December 2018. Every shoulder arthroplasty patient consented to data sharing and all data was collected using standardized forms according to an Institutional Review Board (IRB)-approved protocol.

In some embodiments, to ensure a homogenous dataset, patients with revisions, a diagnosis of humeral fracture, and hemiarthroplasty cases were excluded. Patients with a less than 3 months follow-up were also excluded. These criteria may result in pre-operative, intra-operative, and post-operative data from 5,774 patients with 17,427 post-operative follow-up visits available to train and generate algorithms that predict post-operative scores of the: ASES, UCLA, and Constant metrics, the global shoulder function score (0=no mobility and 10=normal), the VAS pain score (0=no pain and 10=extreme pain), active abduction (0°-180° arm elevation in the frontal plane), active forward elevation (0°-180° arm elevation in the sagittal plane), and/or active external rotation (−90 to 90° with the arm at the side) at 3-6 months, 6-9 months, 1 year [9-18 months], 2-3 years [18-36 months], 3-5 years [36-60 months], and 5+ years [60+ months]. An active range of motion was measured with a goniometer at each patient clinical visit.

In some embodiments, the predictive algorithms may be trained and generated using demographic data, diagnoses, comorbidities, implant type, pre-operative ROM, pre-operative radiographic findings, and pre-operative PROM scores (such as the ASES, SPADI, SST, UCLA, and Constant metrics), including the individual questions used to derive each score; in total, 291 labeled features were utilized. The clinical data from 2,153 primary aTSA patients (7,305 visits; average follow-up=26.7 months) and 3,621 primary rTSA patients (10,122 visits; average follow-up=22.8 months) was used to train and generate the predictive models at each post-surgical timepoint: 3-6 months (aTSA=1282 and rTSA=2227 visits), 6-9 months (aTSA=658 and rTSA=1177 visits), 1 year (aTSA=1451 and rTSA=2445 visits), 2-3 years (aTSA=1347 and rTSA=1882 visits), 3-5 years (aTSA=1321 and rTSA=1482 visits), and 5+ years (aTSA=1246 and rTSA=907 visits). A random selection of 66.7% of this data defined the training cohort and the remaining 33.3% defined the validation test cohort, which was used to evaluate the prediction error of each algorithm.

In some embodiments, the predictive models may include three trained supervised machine learning techniques: 1) linear regression, 2) XGBoost, and 3) Wide and Deep.

As a general technical background to these predictive models, a linear regression model assumes and models a linear relationship between the pre-operative data (input variables) and the outcomes data (output variable) from the full training dataset. An XGBoost model is an ensemble method of multiple regression-trees. These regression-trees may be built by iteratively partitioning the entire training dataset into multiple small batches using a method called boosting. XGBoost may handle missing-values and data-sparsity relatively well. The Wide and Deep model is a hybrid of the linear regression model and a deep-learning model that is particularly useful for classification problems with sparse inputs. The features in the clinical outcome database 62 may be categorical, so the Wide and Deep model may be well suitable to this technique.

In some embodiments, the deep-learning component may utilize a layered function that computes the model coefficients based upon inputs from a previous layer, ultimately propagating those coefficients to the top-layer of the outcome prediction model. The wide (or linear component) may be used for dense/numeric features while the deep (or feed-forward neural network component) may used for sparse/categorical features. A baseline average analysis as the study control may be used to evaluate the relative accuracy of each predictive model.

FIG. 5 is a table showing minimally clinically important difference (MCID) and substantial clinical benefit (SCB) thresholds for each outcome metric (measure) for the overall cohort, aTSA, and rTSA, in accordance with one or more embodiments of the present disclosure. The primary target of each model may be used to predict the post-operative outcome measure at each post-surgical timepoint. The secondary targets may be identified if a patient would experience clinical improvement greater than the MCID and SCB patient satisfaction anchor-based thresholds for each measure previously established by Simovitch et al. referring to FIG. 5. MCID may represent the floor threshold for improvement and may define the minimum improvement that a patient perceives as a meaningful change by a given treatment. SCB may differ from MCID in that it may represent the target level of improvement for achieving a substantial benefit as perceived by the patient.

In some embodiments, the predictive performance of the primary target of each model may be quantified by the Mean Absolute Error (MAE) between the actual and predicted values for each outcome measure for aTSA and rTSA patients in the 33.3% validation test cohort. To aid in model interpretability, an F-score from the XGBoost model may be used to identify the most-predictive features. The F-score may quantify the frequency that a particular feature may be used as a candidate for a split in the decision-tree algorithm. The performance of the secondary target, or the accuracy of each model to identify if a patient will achieve the MCID and SCB improvement thresholds for each outcome measure at 2-3 years follow-up may be quantified using the classification metrics of precision for quantifying the ability for a model to not identify a negative as positive, recall for quantifying the ability for a model to identify a positive as a positive, F1-score for quantifying the harmonic mean between the precision and recall scores, accuracy for quantifying the ratio of the correct predictions to the total number of predictions, and/or the Area Under the Receiver Operating Curve (AUROC), all of which may determine the overall accuracy of the model. The results of these predictive models are tabulated below.

Figure 6:
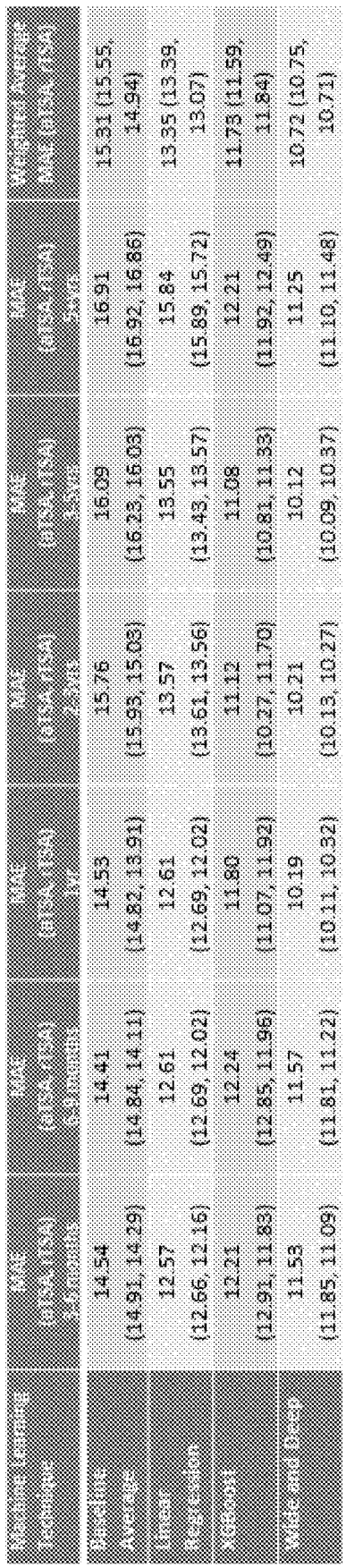
FIG. 6 is a table showing a comparison of Mean Absolute Error (MAE) associated with American Shoulder and Elbow Surgeons Shoulder Score (ASES) Prediction Models in accordance with one or more embodiments of the present disclosure.

FIG. 6 is a table showing a comparison of Mean Absolute Error (MAE) associated with American Shoulder and Elbow Surgeons Shoulder Score (ASES) Prediction Models in accordance with one or more embodiments of the present disclosure.

FIG. 7 is a table showing a comparison of Mean Absolute Error (MAE) associated with University of California, Los Angeles (UCLA) Prediction Models in accordance with one or more embodiments of the present disclosure.

FIG. 8 is a table showing a comparison of Mean Absolute Error (MAE) associated with Constant Prediction Models in accordance with one or more embodiments of the present disclosure.

FIG. 9 is a table showing a comparison of Mean Absolute Error (MAE) associated with Global Shoulder Function Score Prediction Models in accordance with one or more embodiments of the present disclosure.

Figure 10:
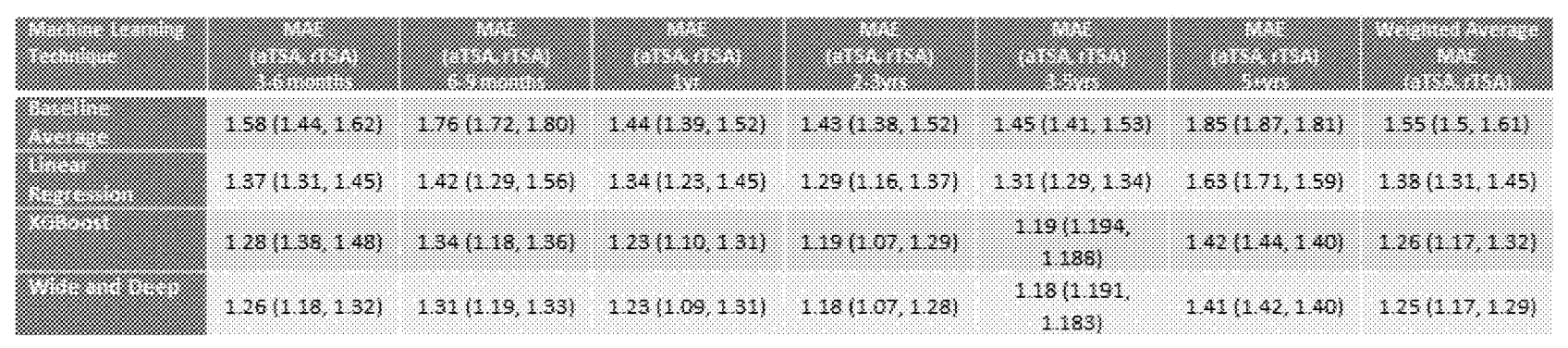

FIG. 10 is a table showing a comparison of Mean Absolute Error (MAE) associated with visual analogue scale (VAS) Pain Score Prediction Models in accordance with one or more embodiments of the present disclosure.

Figure 11:
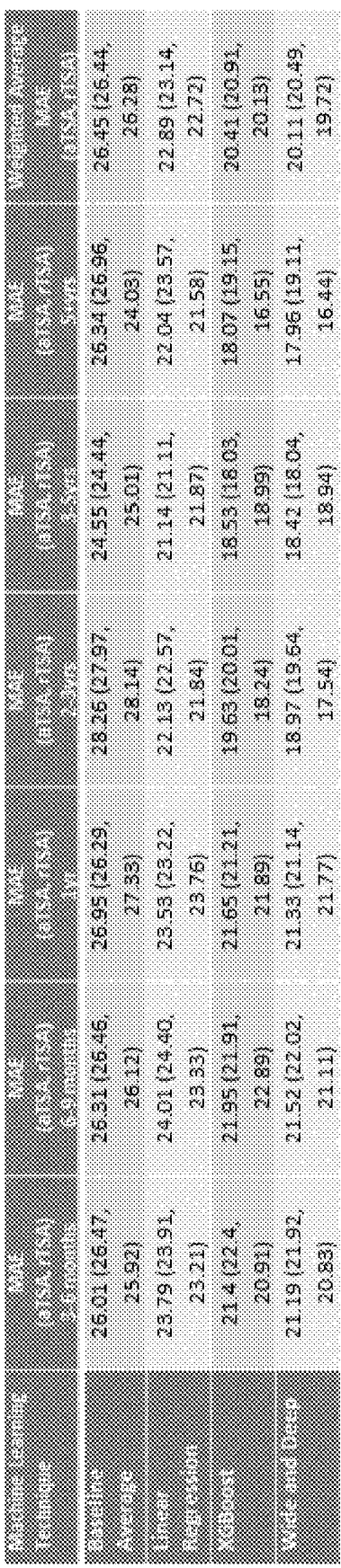
FIG. 11 is a table showing a comparison of Mean Absolute Error (MAE) associated with Active Abduction Prediction Models in accordance with one or more embodiments of the present disclosure.

FIG. 11 is a table showing a comparison of Mean Absolute Error (MAE) associated with Active Abduction Prediction Models in accordance with one or more embodiments of the present disclosure.

FIG. 12 is a table showing a comparison of Mean Absolute Error (MAE) associated with Active Forward Elevation Prediction Models in accordance with one or more embodiments of the present disclosure.

FIG. 13 is a table showing a comparison of Mean Absolute Error (MAE) associated with Active External Rotation Prediction Models in accordance with one or more embodiments of the present disclosure.

The primary target predictions for the ASES (FIG. 6), UCLA (FIG. 7) and Constant (FIG. 8) PROMs, the global shoulder function score (FIG. 9), VAS pain score (FIG. 10), active abduction (FIG. 11), forward elevation (FIG. 12), and external rotation (FIG. 13) at 1 year, 2-3 years, 3-5 years, and 5+ years after aTSA and rTSA as presented in the tables of FIGS. 6-13. The Wide and Deep model had the lowest MAE for every measure at each timepoint, followed by XGBoost, and the linear regression model. In spite of accuracy differences, all three predictive outcome algorithms had lower MAE than the baseline average model.

Based on the average weighted MAE, each machine learning technique was most accurate at predicting the Constant score (±7.56% MAE), followed closely by the UCLA score (±8.16% MAE), and finally the ASES score (±10.45% MAE). Across all post-surgical timepoints analyzed, the average MAE for the Wide and Deep prediction model was ±1.2 for the global shoulder function score, ±1.9 for the VAS pain score, ±19.5° for active abduction, ±15.9° for forward elevation, and ±11.4° for external rotation. Differences between aTSA and rTSA patients were similar, with only minor differences observed between each score, each plane of motion analyzed, and across post-surgical timepoints. Note that other predictive models may be generated using this data and techniques, such as the internal rotation score, visual analogue scale pain, and/or the shoulder arthroplasty smart score.

FIG. 14 is a table showing a comparison of the top five most-predictive features as identified by an XGBoost machine learning algorithm to predict patient reported outcome measures (PROM) as ranked by F-score in accordance with one or more embodiments of the present disclosure. FIG. 15 is a table showing a comparison of the five most-predictive features as identified by an XGBoost machine learning algorithm to predict pain, function, and ROM as ranked by F-score in accordance with one or more embodiments of the present disclosure.

In some embodiments, the top five most-predictive features utilized by the XGBoost predictive models for each PROM (FIG. 14), and pain, function, and ROM measures (FIG. 15) is presented in the tables of FIGS. 14-15. In the examples disclosed in this disclosure, for the 291 features used, XGBoost predictive models yielded excellent agreement in the top five F-score-ranked features, though some differences were observed between the PROM models and the pain, function, and ROM models. Follow-up duration, representing the amount of recovery time after surgery, was identified as the most-predictive feature used in all models.

In some embodiments, with regard to the PROMs, two different pre-operative PROMs (SPADI and ASES) and four different pre-operative measures of active ROM were also observed to be highly predictive, along with the categorical question: "Is surgery on dominant hand?". Concerning the pain, function, and ROM measures, the categorical question: "Is surgery on dominant hand?" was identified as the second most-predictive feature in all models. The categorical question: "Is gender female?" was identified as the third most-predictive feature in all models but one. Other highly predictive features were: the pre-operative SPADI score, two different pre-operative measures of active ROM, and a categorical question: "Did patient have previous shoulder surgery?".

Figure 16:
FIG. 16 is a table showing a comparison of the accuracy of an XGBoost Algorithm to predict aTSA and rTSA Patients that experienced a clinical improvement exceeding the MCID threshold for each of the ASES, UCLA, and Constant Scores in accordance with one or more embodiments of the present disclosure.

FIG. 16 is a table showing a comparison of the accuracy of an XGBoost Algorithm to predict aTSA and rTSA Patients that experienced a clinical improvement exceeding the MCID threshold for each of the ASES, UCLA, and Constant Scores in accordance with one or more embodiments of the present disclosure.

Figure 17:
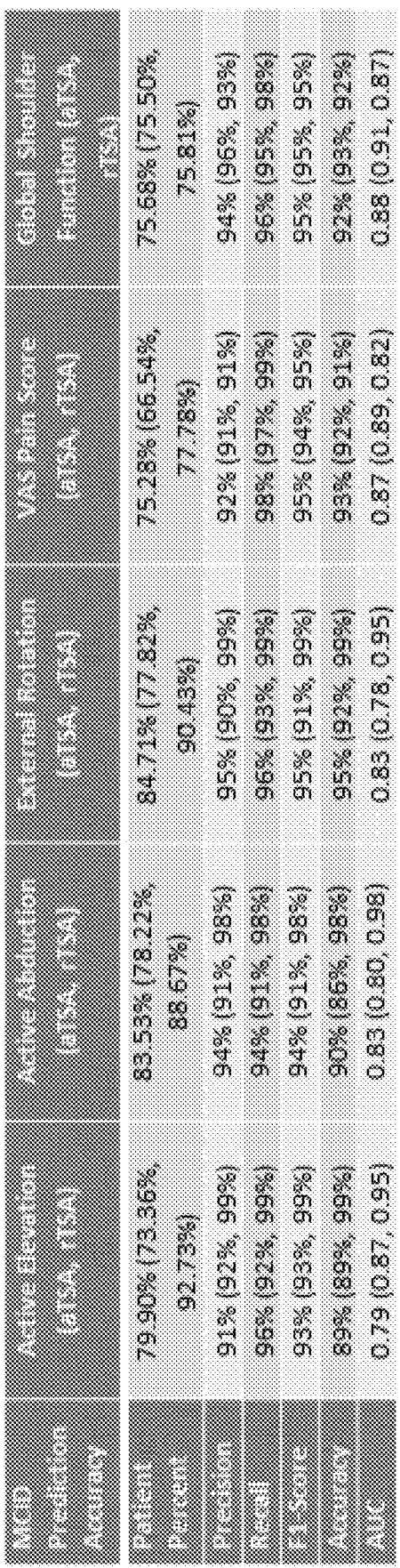
FIG. 17 is a table showing a comparison of the accuracy of an XGBoost Algorithm to predict aTSA and rTSA Patients that experienced a clinical improvement exceeding the MCID threshold for each of the Global Shoulder Function and VAS Pain Scores for Active Abduction, Forward Elevation, and External Rotation ROM Measures in accordance with one or more embodiments of the present disclosure.

FIG. 17 is a table showing a comparison of the accuracy of an XGBoost Algorithm to predict aTSA and rTSA Patients that experienced a clinical improvement exceeding the MCID threshold for each of the Global Shoulder Function and VAS Pain Scores for Active Abduction, Forward Elevation, and External Rotation ROM Measures in accordance with one or more embodiments of the present disclosure.

Figure 18:
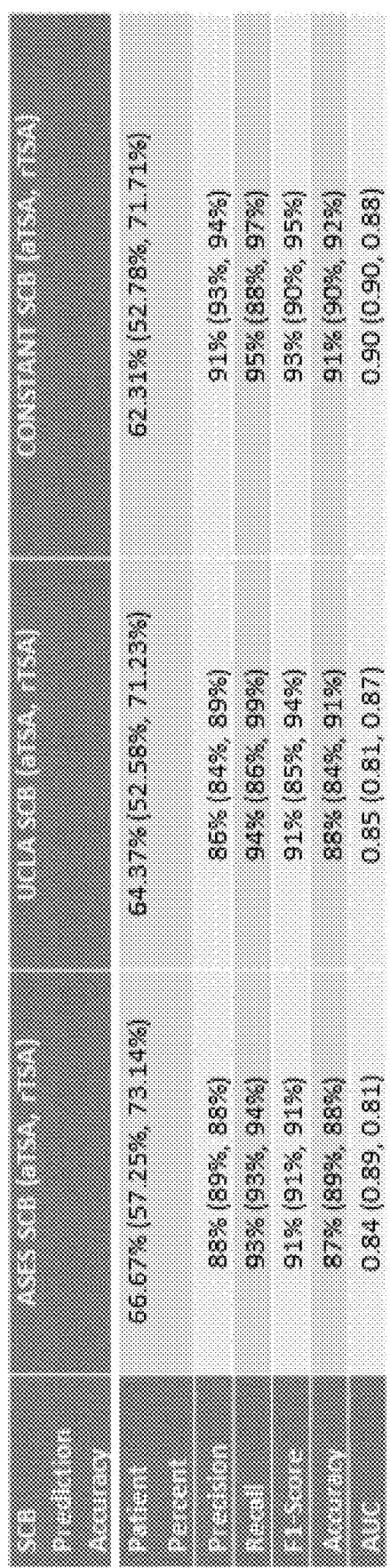
FIG. 18 is a table showing a comparison of the accuracy of an XGBoost Algorithm to predict aTSA and rTSA Patients that experienced a clinical improvement exceeding the SCB threshold for each of the ASES, UCLA, and Constant Scores in accordance with one or more embodiments of the present disclosure.

FIG. 18 is a table showing a comparison of the accuracy of an XGBoost Algorithm to predict aTSA and rTSA Patients that experienced a clinical improvement exceeding the SCB threshold for each of the ASES, UCLA, and Constant Scores in accordance with one or more embodiments of the present disclosure.

Figure 19:
FIG. 19 is a table showing a comparison of the accuracy of an XGBoost Algorithm to predict aTSA and rTSA Patients that experienced a clinical improvement exceeding the SCB threshold for each of the Global Shoulder Function and VAS Pain Scores, and for Active Abduction, Forward Elevation, and External Rotation ROM Measures in accordance with one or more embodiments of the present disclosure.

FIG. 19 is a table showing a comparison of the accuracy of an XGBoost Algorithm to predict aTSA and rTSA Patients that experienced a clinical improvement exceeding the SCB threshold for each of the Global Shoulder Function and VAS Pain Scores, and for Active Abduction, Forward Elevation, and External Rotation ROM Measures in accordance with one or more embodiments of the present disclosure.

In some embodiments, the secondary target MCID predictions for the PROM models (FIG. 16) and the pain, function, and ROM models (FIG. 17) at 2-3 years follow-up is presented in the tables of FIGS. 16-17. The XGBoost PROM models yielded 93-95% accuracy in MCID with an AUROC between 0.87-0.94 for aTSA patients and 93-99% accuracy in MCID with an AUROC between 0.85-0.97 for rTSA patients. In other embodiments, the XGBoost pain/function/ROM models yielded 85-94% accuracy in MCID with an AUROC between 0.79-0.91 for aTSA patients and 90-94% accuracy in MCID with an AUROC between 0.78-0.90 for rTSA patients.

In some embodiments, the SCB predictions for the PROM models (FIG. 18) and the pain, function, and ROM models (FIG. 19) at 2-3 years follow-up is presented in the tables of FIGS. 18-19. The XGBoost PROM models yielded 82-90% accuracy in SCB with an AUROC between 0.80-0.90 for aTSA patients and 87-93% accuracy in SCB with an AUROC between 0.81-0.89 for rTSA patients. In other embodiments, the XGBoost pain/function/ROM models yielded 76-89% accuracy in SCB with an AUROC between 0.73-0.86 for aTSA patients and 88-90% accuracy in SCB with an AUROC between 0.77-0.88 for rTSA patients.

In some embodiments, the predictive outcome analysis may demonstrate the efficacy of multiple machine learning techniques to generate models that accurately predict three PROM scores, pain and function scores, and three active ROM measures at numerous post-surgical follow-up timepoints for both aTSA and rTSA. Prediction accuracy for PROMs, pain relief, and function were similar between aTSA and rTSA patients at each timepoint were analyzed. The Wide and Deep technique consistently demonstrated the best overall predictive performance. Most significantly, these models may risk-stratify patients by accurately identifying patients at the greatest risk for poor outcomes (e.g., failure to achieve MCID thresholds) and accurately identifying patients most likely to achieve excellent outcomes (e.g., to achieve SCB thresholds).

However, the use of 291 exemplary variable inputs used in these shoulder arthroplasty examples may not be a practical tool for an orthopedic surgeon to use in clinic, given the large data-input and time burden on the surgeon and patient. In a review of the F-score results of this analysis and the application of extensive domain knowledge related to total shoulder arthroplasty, an abbreviated model was generated which requires only 10-20% of the original model inputs Thus, a clinical deployment of such a software predictive outcome tool may be more practical for the orthopedic surgeon to use in clinic, without sacrificing the predictive accuracy of the model.

FIG. 20 is a table showing a list of predictive model inputs to machine learning models for calculating the Global Shoulder Function Score, the VAS Pain Score, and Active Abduction, Active Forward Elevation, and Active External Rotation in accordance with one or more embodiments of the present disclosure.

FIG. 21 is a table showing a list of additional predictive model inputs to machine learning models for calculating an ASES score in accordance with one or more embodiments of the present disclosure. These are predictive model inputs in addition to what is presented in FIG. 20.

FIG. 22 is a table showing a list of additional predictive model inputs to machine learning models for calculating a Constant Score in accordance with one or more embodiments of the present disclosure. These are predictive model inputs in addition to what is presented in FIG. 20. The Pre-CT planning predictive model and the Post-CT Predictive model of FIGS. 20-22 may be equivalent to the initial Pre-Op Prediction MLM 50 and the Image-Based Prediction MLM 52 in the system 10 of FIG. 1, respectively.

In some embodiments, a three-fold predictive outcomes model, (1. Active ROM, Pain Scores, and Global Shoulder Function Scores=19 user inputs, 2. ASES=10 additional user inputs, and 3. Constant=20 additional user inputs) may be formulated, which may be divided into two steps of generating a first predictive model also referred to herein as an initial preop prediction model using data inputs prior to an image-based (e.g., 3D CT-based) surgical planning step, and generating a second predictive model also referred to herein as a final preop prediction model which includes additional data taken from the image-based (e.g., 3D CT-based) surgical planning step. The data used in the first predictive model may utilize patient demographics, diagnosis, comorbidities, patient history, physician measures of active range of motion, patient-specific answers to a few highly-predictive questions, and also patient-specific answers for the questions composing the ASES and Constant scores. A full list of these questions for these 3-fold outcomes models is demonstrated in the tables of FIGS. 20, 21, and 22, respectively.

In some embodiments, the data used in the second predictive model may utilize outputs from the surgeon directed positioning of the ideal implant size, type, and position to fit the patient's bony anatomy in the image-based (e.g., 3D CT) reconstruction surgical planning step. The proposed workflow describing the flow of the patient from clinic and to surgery, and how these predictive models pre-medical imaging (pre-CT) planning and post medical imaging (post-CT) planning may be utilized to determine the appropriate treatment at each stage is described in FIG. 23.

Figure 23:
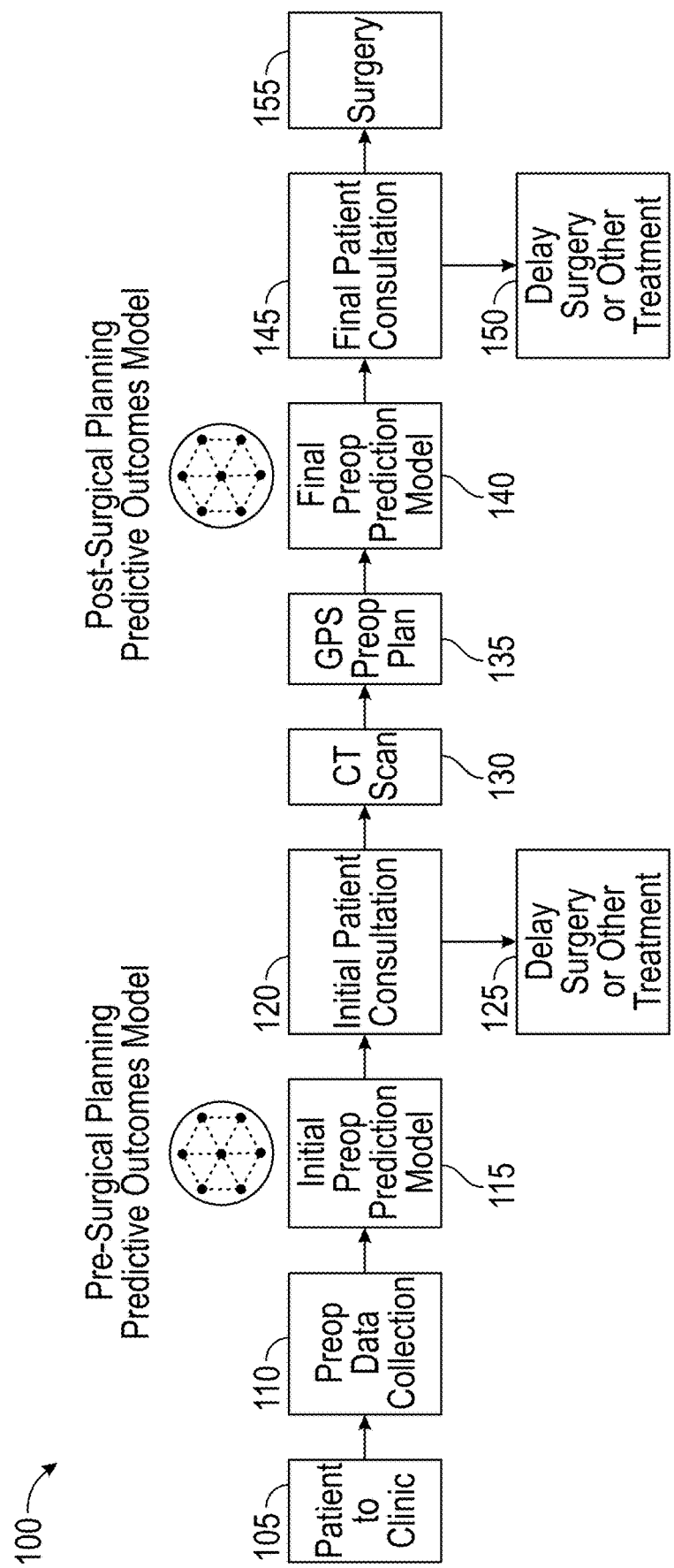
FIG. 23 is an exemplary flow diagram for modeling predictive outcomes of arthroplasty surgical procedures in accordance with one or more embodiments of the present disclosure.

FIG. 23 is an exemplary flow diagram 100 for modeling predictive outcomes of arthroplasty surgical procedures in accordance with one or more embodiments of the present disclosure. The exemplary flow diagram 100 with reference to FIG. 1 may include the patient 25 entering a clinic (step 105) to consult with the doctor 20 about an arthroplasty surgical procedure to improve or replace a joint. The doctor 20 may collect pre-op patient-specific data from the patient 25 that may be entered into the patient-specific data collection module 46 executed by the processor 45 on the computing device 77. Alternatively, and/or optionally, the patient-specific data collection module 46 may query the plurality of N electronic resources (40A and 40B) for patient-specific pre-operative data that may be received by the server 15 over the communication network 30. The received dataset may include pre-operative patient specific data for an arthroplasty surgery to be performed on a joint of a patient where the pre-operative patient specific data may further include a medical history of the patient, a measured range of movement for at least one type of joint movement, at least one pain metric associated with the joint, or any combination thereof.

In some embodiments, the received pre-operative patient specific data may be inputted to an initial preop prediction machine learning model (MLM) 115 (e.g., the initial preop prediction MLM 50 of FIG. 1) also referred to herein as a first machine learning model.

In some embodiments, the initial preop prediction MLM 115 may determine a first predicted post-operative joint performance data output that includes at least one first predicted post-operative performance metric of the joint, which may then be displayed on the display of the computing device 77 to a user, such as the doctor 20, for example.

In some embodiments, the doctor 20 and the patient 25 may have an initial patient consultation 120. The doctor 20 and/or the patient 25 may decide to continue with the arthroplasty surgery of the joint, or to delay the surgery or to pursue other treatment 125 for the diseased joint.

In some embodiments, the doctor 20 may request that the patient 25 may receive at least one medical image of the joint, such as a computerized tomography (CT) scan 130, obtained from at least one medical imaging procedure performed on the patient 25. The at least one medical image of the joint may include an X-ray image, a computerized tomography (CT) image, a magnetic resonance image, a three-dimensional (3D) image, and/or a 3D medical image based on multiple X-ray images. The at least one medical image of the joint may also include images of the bones and/or the connective tissues attached to and/or forming the joint.

In some embodiments, in a guided personalized surgery (GPS) Preop Planning 135 step, the CT image-based (GPS) Joint Reconstruction Planning module 48, which may be a software program executed by the processor 45 on the server 15, may generate a reconstruction plan of the joint that is display on the GUI 75. The CT image-based (GPS) Joint Reconstruction Planning module 48 may also be referred to herein as the GPS Planning Software as in FIG. 20.

In some embodiments, the reconstruction plan may utilize at least one arthroplasty surgical parameter chosen by the doctor in response to the doctor viewing the first predicted post-operative joint performance data output. The reconstruction plan may include at least one arthroplasty surgical parameter that is selected from, but not limited to, at least one implant, at least one implant size, at least one arthroplasty surgical procedure, and/or at least one position for implanting the at least one implant in the joint. The reconstruction plan may include different views of the at least one medical image of the joint, such as the CT scan 130, that may be displayed on the GUI 75 along with images of the at least one implant implanted in the joint. In other embodiments, for the case of shoulder arthroplasty, the at least one arthroplasty surgical parameter may also include any of the user inputs from the GPS Planning Software as shown in the table of FIG. 20.

In some embodiments, the at least one arthroplasty surgical parameter may be inputted to a final Preop prediction model 140 (e.g., the image-based prediction MLM 52 of FIG. 1) also referred to herein as a second machine learning model. The at least one arthroplasty surgical parameter may include any of the data inputs to the Post-CT Planning Predictive Model (e.g., final Preop prediction model 140) such as shown in the table of FIG. 20, for example, for shoulder arthroplasty. In other embodiments, the data inputs to the second machine learning model may include any of the inputs to the first machine learning model as well as any suitable parameters extracted from the reconstruction plan. In some embodiments, the first machine learning model (e.g., the initial preop prediction MLM 115) and the second machine learning model (e.g., final Preop prediction model 140) may be the same machine learning model.

In some embodiments, a software application for modeling the predictive outcomes of arthroplasty surgical procedures executed by the processor 45 may include any or all of the software modules: the patient-specific data collection module 46, the CT image-based guided personalized surgery (GPS) Joint Reconstruction Planning module 48, the initial pre-op prediction machine learning model (MLM) module 50, the image-based Prediction MLM module 52, the machine learning model training module 54, and/or the GUI manager module 56. In other embodiments, the initial pre-op prediction machine learning model (MLM) module 50 and the image-based Prediction MLM module 52 may be the same machine learning model.

In some embodiments, the software application for modeling the predictive outcomes of arthroplasty surgical procedures may be executed by the processor 45 and the GUI manager 56 may remotely control the GUI 75 running on the computing device 77 for providing inputs and/or outputs from the server 15.

In some embodiments, the first predicted post-operative joint performance data output and/or the second predicted post-operative joint performance data output may be displayed on the GUI 75 to the doctor 20 in any suitable format, such as outputting a list of predicted post-operative outcome metrics of the joint based on data inputs such as pre-operative patient specific data, medical images of the joint, and arthroplasty surgical parameters to the predictive outcome machine learning models. A visual representation of the implant implanted in a joint based on the medical images of the joint. The visual representation of the implant implanted in a joint may include raw, enhanced, and/or augmented images of the joint that may be displayed on GUI 75.

In some embodiments, the second predicted post-operative joint performance data output may include displaying on the GUI 75 at least one arthroplasty surgery recommendation of combinations of surgical procedures, implant types, implant sizes, implant positions along with the predicted post-operative outcome metrics from the models for each combination so as to allow the surgeon to optimize the post-operative joint performance by varying the arthroplasty surgical parameters. This optimization may be performed before and/or during the surgery.

In some embodiments, the at least one arthroplasty surgery recommendation may include a recommendation not to proceed with the arthroplasty surgical procedure and/or to pursue another treatment.

In some embodiments, the final Preop prediction model 140 may determine a second predicted post-operative joint performance data output that includes the at least one second predicted post-operative performance metric of the joint, which may then be displayed on the GUI 75 of the computing device 77 to a user, such as the doctor 20, for example.

In some embodiments, the doctor 20 may review second predicted post-operative joint performance data output and conduct a final patient consultation 145 with the patient 25. The doctor 20 and/or the patient 25 may decide to schedule the arthroplasty surgery 155 of the joint, or to delay the surgery or to pursue other treatment 150 for the diseased joint.

Figure 24:
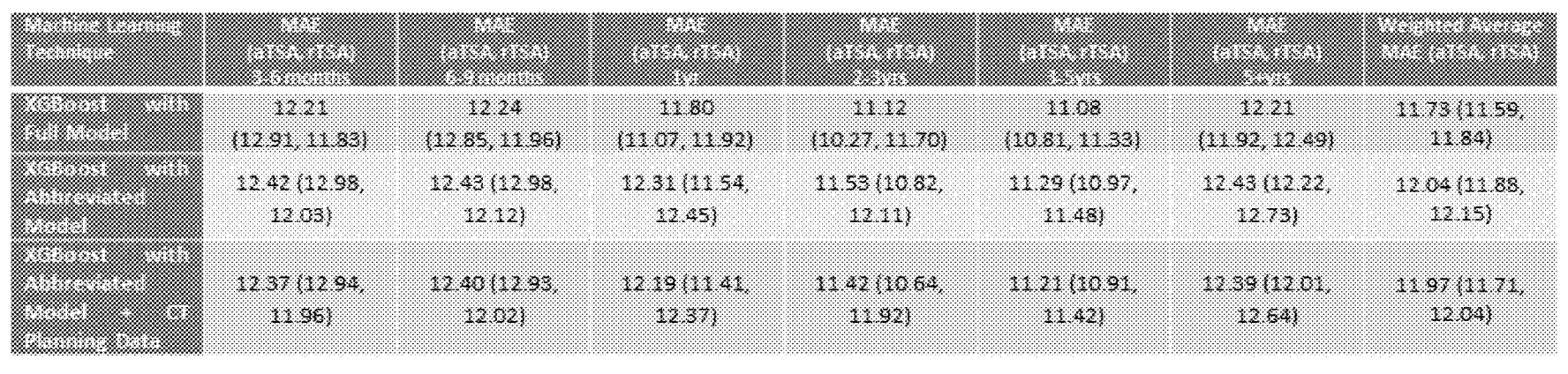

FIG. 24 is a table showing a comparison of Mean Absolute Error (MAE) associated with the ASES predictions using the Full and Abbreviated XGBoost machine learning models in accordance with one or more embodiments of the present disclosure.

FIG. 25 is a table showing a comparison of Mean Absolute Error (MAE) associated with the constant predictions using the Full and Abbreviated XGBoost machine learning models in accordance with one or more embodiments of the present disclosure.

Figure 26:
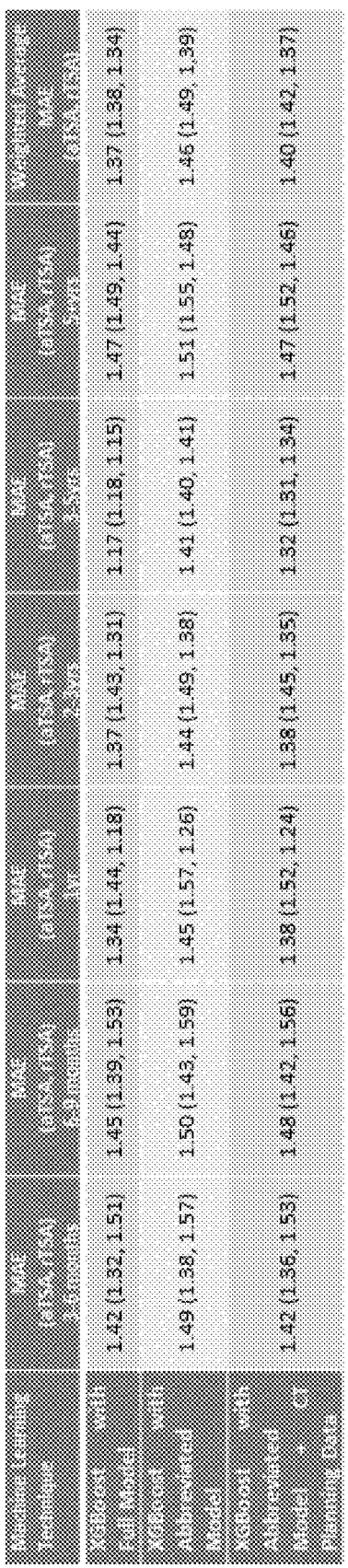
FIG. 26 is a table showing a comparison of Mean Absolute Error (MAE) associated with the Global Shoulder Function Score Predictions using the Full and Abbreviated XGBoost machine learning models in accordance with one or more embodiments of the present disclosure.

FIG. 26 is a table showing a comparison of Mean Absolute Error (MAE) associated with the Global Shoulder Function Score Predictions using the Full and Abbreviated XGBoost machine learning models in accordance with one or more embodiments of the present disclosure.

Figure 27:
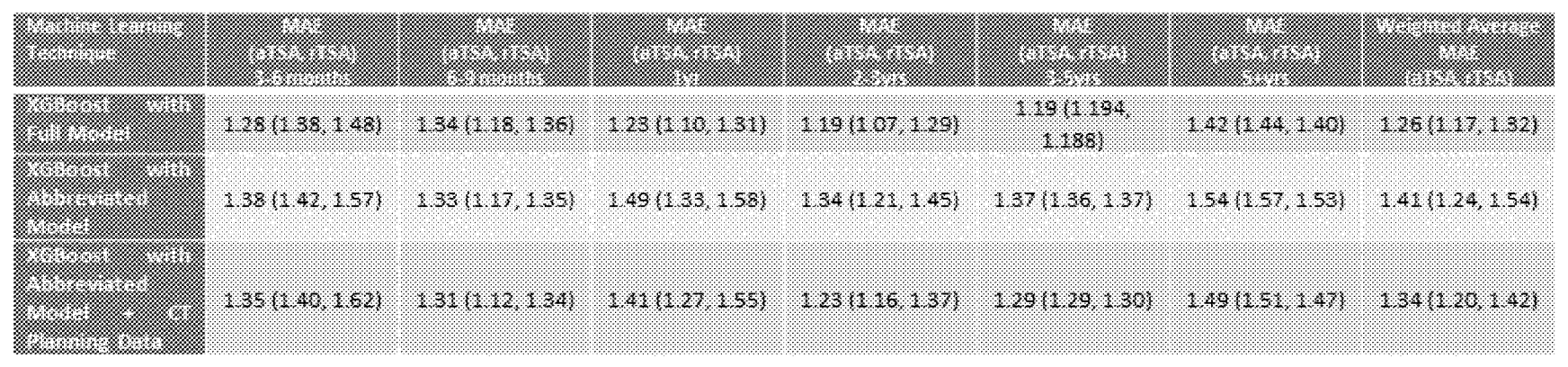

FIG. 27 is a table showing a comparison of Mean Absolute Error (MAE) associated with the VAS Pain Score Predictions using the Full and Abbreviated XGBoost machine learning models in accordance with one or more embodiments of the present disclosure.

Figure 28:
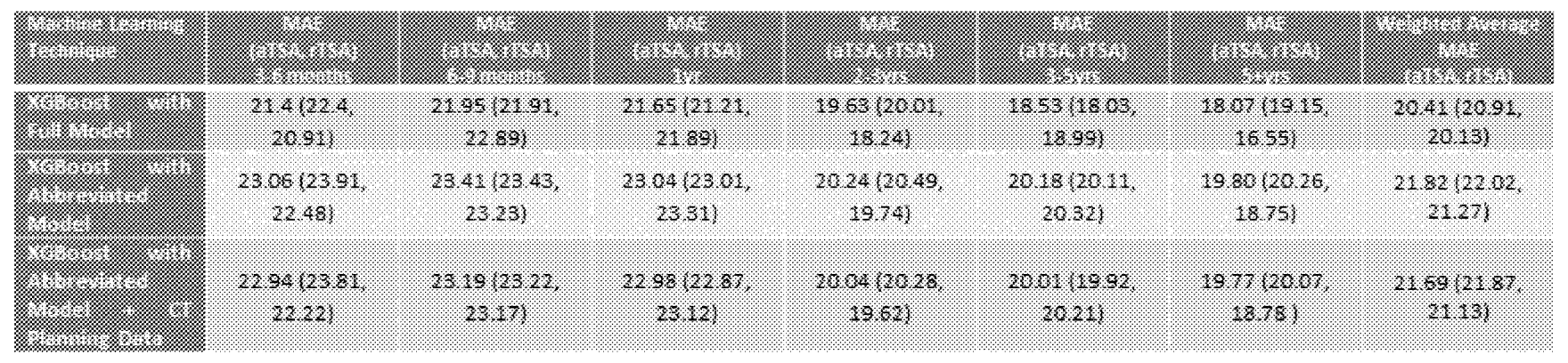

FIG. 28 is a table showing a comparison of Mean Absolute Error (MAE) associated with the Active Abduction Predictions using the Full and Abbreviated XGBoost machine learning models in accordance with one or more embodiments of the present disclosure.

FIG. 29 is a table showing a comparison of Mean Absolute Error (MAE) associated with the Active Forward Elevation Predictions using the Full and Abbreviated XGBoost machine learning models in accordance with one or more embodiments of the present disclosure.

Figure 30:
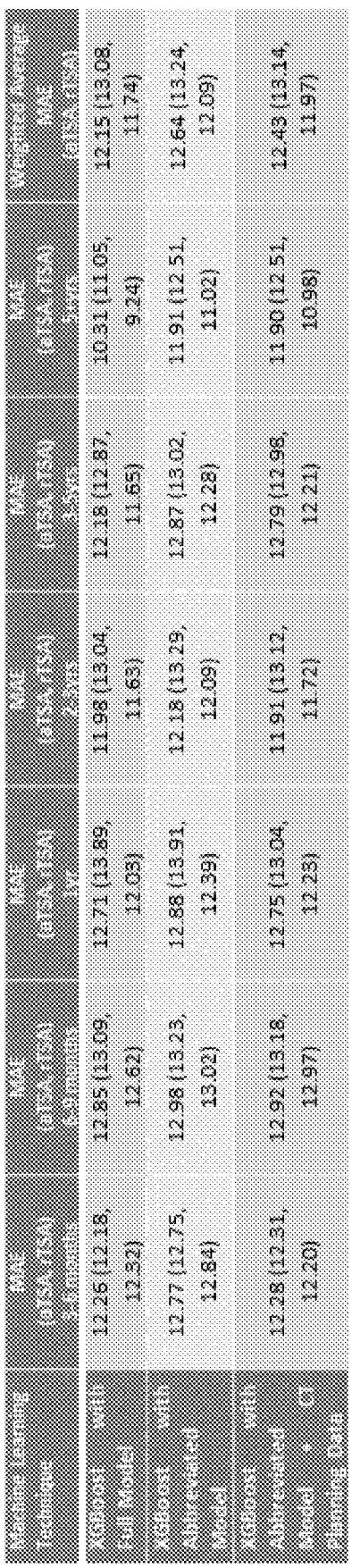
FIG. 30 is a table showing a comparison of Mean Absolute Error (MAE) associated with the Active External Rotation Predictions using the Full and Abbreviated XGBoost machine learning models in accordance with one or more embodiments of the present disclosure.

FIG. 30 is a table showing a comparison of Mean Absolute Error (MAE) associated with the Active External Rotation Predictions using the Full and Abbreviated XGBoost machine learning models in accordance with one or more embodiments of the present disclosure.

FIG. 31 is a table showing a comparison of a full XGBoost model predictions for aTSA and rTSA patients that experienced a clinical improvement exceeding the MCID threshold for multiple different outcome measures in accordance with one or more embodiments of the present disclosure.

Figure 32:
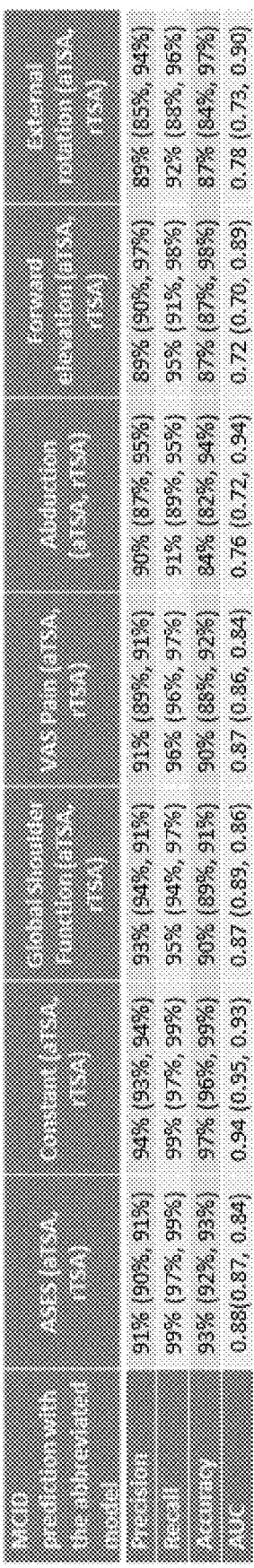
FIG. 32 is a table showing a comparison of an abbreviated XGBoost model predictions for aTSA and rTSA patients that experienced a clinical improvement exceeding the MCID threshold for multiple different outcome measures in accordance with one or more embodiments of the present disclosure.

FIG. 32 is a table showing a comparison of an abbreviated XGBoost model predictions for aTSA and rTSA patients that experienced a clinical improvement exceeding the MCID threshold for multiple different outcome measures in accordance with one or more embodiments of the present disclosure.

FIG. 33 is a table showing a comparison of a full XGBoost model predictions for aTSA and rTSA patients that experienced a clinical improvement exceeding the SCB threshold for multiple different outcome measures in accordance with one or more embodiments of the present disclosure.

Figure 34:
FIG. 34 is a table showing a comparison of an abbreviated XGBoost model predictions for aTSA and rTSA patients that experienced a clinical improvement exceeding the SCB threshold for multiple different outcome measures in accordance with one or more embodiments of the present disclosure.

FIG. 34 is a table showing a comparison of an abbreviated XGBoost model predictions for aTSA and rTSA patients that experienced a clinical improvement exceeding the SCB threshold for multiple different outcome measures in accordance with one or more embodiments of the present disclosure.

Figure 35:
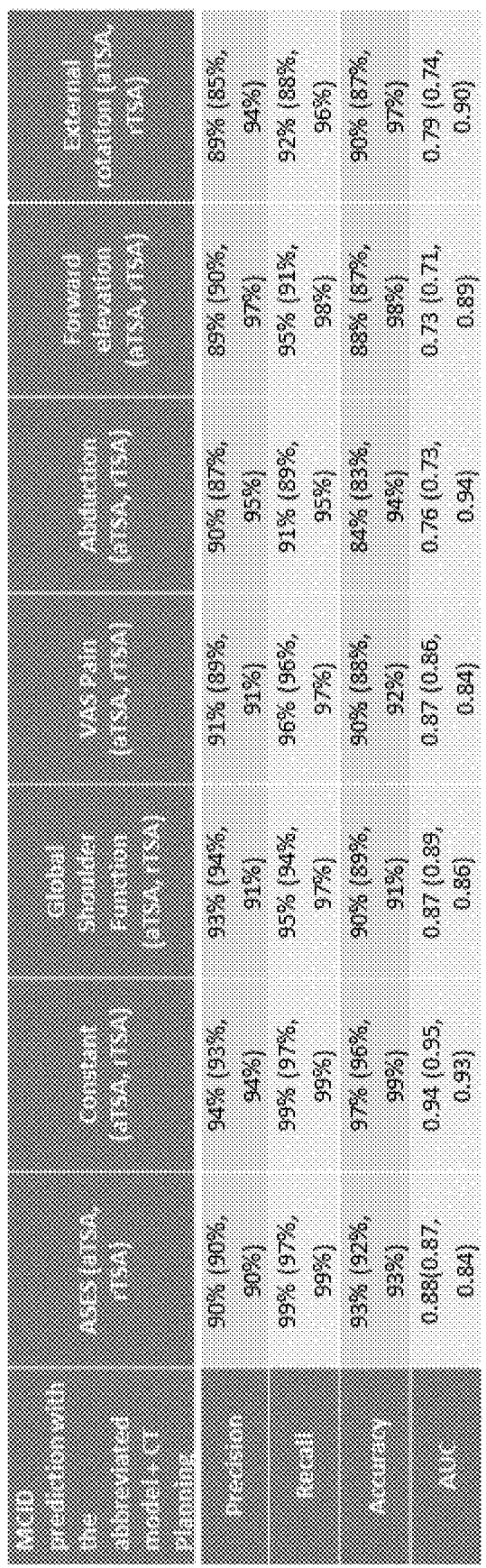
FIG. 35 is a table showing a comparison of an abbreviated XGBoost model with inputs from CT planning data to make predictions for aTSA and rTSA patients that experienced a clinical improvement exceeding the MCID threshold for multiple different outcome measures in accordance with one or more embodiments of the present disclosure.

FIG. 35 is a table showing a comparison of an abbreviated XGBoost model with inputs from CT planning data to make predictions for aTSA and rTSA patients that experienced a clinical improvement exceeding the MCID threshold for multiple different outcome measures in accordance with one or more embodiments of the present disclosure.

FIG. 36 is a table showing a comparison of an abbreviated XGBoost model with inputs from CT planning data to make predictions for aTSA and rTSA patients that experienced a clinical improvement exceeding the SCB threshold for multiple different outcome measures in accordance with one or more embodiments of the present disclosure.

In some embodiments, the model inputs (in the pre-planning and post-planning phases of the predictive models) may be the most highly-predictive parameters, which may provide very similar levels of predictive accuracy similar to the case of using all variables in the clinical outcome database 62. As demonstrated in the tables of FIGS. 24-30, the results of the abbreviated model may yield nearly identical accuracy for each outcome metric as the predictive model which data inputs from the entire the clinical outcome database 62.

In some embodiments, the prediction accuracy between aTSA and rTSA were observed to be similar, for both the full and abbreviated models. Additionally, for both the full and abbreviated prediction models, MAE was found to be slightly higher at earlier post-operative timepoints than at later post-operative timepoints. Across all post-operative timepoints analyzed, the average difference in MAE between the full and abbreviated model predications was found to be ±0.3 MAE for the ASES score (±0.3 aTSA and ±0.4 rTSA), ±0.9 for the Constant score (±0.7 aTSA and ±0.8 rTSA), ±0.1 for the Global Shoulder Function score (±0.1 aTSA and ±0.1 rTSA), ±0.1 for the VAS pain score (±0.0 aTSA and ±0.2 rTSA), ±1.4° for abduction (±1.1 aTSA and ±1.2 rTSA), ±1.6° for forward elevation (±1.7 aTSA and ±1.4 rTSA), and ±0.4° for external rotation (±0.1 aTSA and ±0.4 rTSA).

In some embodiments, as demonstrated in the tables of FIGS. 31-34, the abbreviated models yielded nearly-identical MCID and SCB accuracy results as well, demonstrating the ability of these models to effectively risk-stratify patients prior to surgery based upon their ability to achieve varying magnitudes of improvement at 2-3 years of follow-up according to multiple different outcome metrics.

In some embodiments, specifically regarding the MCID, the full predictive models achieved 82-96% accuracy in MCID with an AUROC between 0.75-0.97 for aTSA patients; whereas, the abbreviated predictive models achieved 82-96% accuracy in MCID with an AUROC between 0.70-0.95 for aTSA patients. The full predictive models achieved 91-99% accuracy in MCID with an AUROC between 0.82-0.98 for rTSA patients; whereas, the abbreviated predictive models achieved 91-99% accuracy in MCID with an AUROC between 0.84-0.94 for rTSA patients.

In some embodiments, similarly regarding the SCB, the full predictive models achieved 79-90% accuracy in SCB with an AUROC between 0.74-0.90 for aTSA patients; whereas, the abbreviated predictive models achieved 76-90% accuracy in SCB with an AUROC between 0.70-0.89 for aTSA patients. Finally, the full predictive models achieved 83-92% accuracy in SCB with an AUROC between 0.78-0.88 for rTSA patients; whereas, the abbreviated predictive models achieved 81-90% accuracy in SCB with an AUROC between 0.70-0.87 for rTSA patients. With regard to the interpretation of AUROC values used in these MCID and SCB predictions, 0.5 is considered random, >0.7 is considered acceptable, >0.8 is considered good, and >0.9 is considered excellent discrimination for a predictive model.

In some embodiments, for the abbreviated model algorithms, the average MCID AUROC values were 0.82 for aTSA and 0.89 for rTSA and the average SCB AUROC values were 0.85 for aTSA and 0.82 for rTSA, suggesting these algorithms generated from a minimal feature set exhibit on average, between good and excellent discrimination, and at worst, acceptable discrimination. These abbreviated model prediction values may be improved by adding in the selected implant data from the guided personalized surgery (GPS) CT planning, as demonstrated in the tables of FIGS. 24-30 and 35-36. Note that other predictive models may be generated using this data and the techniques disclosed herein, such as the internal rotation score, visual analogue pain at worst, and also the shoulder arthroplasty smart score.

FIG. 24 is a table showing a comparison of Mean Absolute Error (MAE) associated with the ASES predictions using the Full and Abbreviated XGBoost machine learning models in accordance with one or more embodiments of the present disclosure.

FIG. 25 is a table showing a comparison of Mean Absolute Error (MAE) associated with the constant predictions using the Full and Abbreviated XGBoost machine learning models in accordance with one or more embodiments of the present disclosure.

FIG. 26 is a table showing a comparison of Mean Absolute Error (MAE) associated with the Global Shoulder Function Score Predictions using the Full and Abbreviated XGBoost machine learning models in accordance with one or more embodiments of the present disclosure.

FIG. 27 is a table showing a comparison of Mean Absolute Error (MAE) associated with the VAS Pain Score Predictions using the Full and Abbreviated XGBoost machine learning models in accordance with one or more embodiments of the present disclosure.

FIG. 28 is a table showing a comparison of Mean Absolute Error (MAE) associated with the Active Abduction Predictions using the Full and Abbreviated XGBoost machine learning models in accordance with one or more embodiments of the present disclosure.

FIG. 29 is a table showing a comparison of Mean Absolute Error (MAE) associated with the Active Forward Elevation Predictions using the Full and Abbreviated XGBoost machine learning models in accordance with one or more embodiments of the present disclosure.

FIG. 30 is a table showing a comparison of Mean Absolute Error (MAE) associated with the Active External Rotation Predictions using the Full and Abbreviated XGBoost machine learning models in accordance with one or more embodiments of the present disclosure.

Thus, the machine learning predictive models described herein may effectively provide the same predictive accuracy of for clinical outcomes for aTSA and rTSA, for a given patient prior to arthroplasty surgery based on using more than 75% less user inputs for the abbreviated prediction model than the full prediction model. This large reduction in the user input data enables the use of such a tool in a surgeon's clinic, as it requires a similar burden of inputs as other commonly used patient reported outcome metrics to quantify clinical results after aTSA and rTSA.

In some embodiments, the machine learning models used in the software application may be abbreviated machine learning models so as to improve the computation efficiency and/or to enhance the computing speed of the server 15 as demonstrated in the tables of the previous figures.

Stated differently, the initial preop prediction MLM 50 and the image-based prediction MLM 52 may be abbreviated machine learning models that may be referred to respectively herein as the first abbreviated MLM and the second abbreviated MLM In some embodiments, in addition to the outcome metrics and range of motion predictions, the predictive outcome models may identify the factors that are driving the prediction up and down. Specifically, for those factors which are modifiable by the patient, the predictive outcome models may provide recommendations to the patient on what they can do to improve the outcomes prediction in order to make the patient a more active participant in the surgeon-patient consultation.

In some embodiments, the predictive outcome models may incorporate a look-up table of typical complication rates that may be associated with aTSA and rTSA for a given patients demographics, diagnosis, patient hi story, and/or comorbidities.

In some embodiments, the predictive outcome models may provide additional features to the surgeon which may assist in achieving better predicted outcomes. For example, if the case was navigated, the outcomes could be improved by 2%, or as another illustrative example, if a patient has 10 degrees of glenoid retroversion, a better outcome may be predicted using an augmented glenoid component for aTSA and/or rTSA as opposed to a standard component (with or without eccentric glenoid reaming surgical techniques).

In some embodiments, trade-offs between implant technique may be implemented in order to help the surgeon user improve their decision making. For example, to inform surgeons when to use aTSA versus rTSA for patients with different rotator cuff tear sizes, to inform surgeons when to use aTSA versus rTSA for different Goutallier rotator cuff fatty infiltration grades, to inform surgeons when to use bone graft versus augmented glenoid components for different glenoid deformity classification types (such as the Walch, Favard, or Antuna) or for a particular glenoid wear measurement (like retroversion, inclination, or beta angle), to inform when to perform eccentric glenoid reaming versus off-axis reaming to correct glenoid wear, and also by how much, and/or to inform when to use a standard length humeral stem versus a short humeral stem versus a stemless humeral implant, and what size of each implant to select based upon bone quality.

In some embodiments, these arthroplasty surgical parameters may be varied on-the-fly to allow the surgeon either before surgery or during surgery to observe these tradeoffs on the software platform in the second predicted post-operative joint performance data output, in response to the surgeon (e.g., the user) varying any of the at least one arthroplasty surgical parameter in the reconstruction plan before the arthroplasty surgery, during the arthroplasty surgery, or both.

In some embodiments, data from early post-surgical follow-up visits, such as 2 weeks, 6 weeks, 8 weeks, 12 weeks, 4 months, or earlier may be used to predict outcomes at different post-surgical timepoints. The benefit of these post-surgical predictions is that they may potentially provide a more accurate estimation of the patient-specific improvement. The data may be a useful aid in establishing more patient-specific rehabilitation protocols targeting improvement in a given metric relative to other outcome metrics.

In some embodiments, this data or additional data (and/or incorporate additional data directly from the patient's electronic medical record or some other database, such as data stored in the cloud and/or generated from wearable device which may measure a patient's movement and/or activity level, may accept responses from patient related to pain levels, etc.) may be used to further refine these predictive models and create more accurate inputs using additional data. The data may also further help risk-stratify patients for shoulder arthroplasty and make recommendations on healthcare workflows, such as identifying patients who may safely have surgery in an ambulatory surgical center. The predictive models may make recommendations regarding whether a specific patient should have in-patient vs. outpatient surgery in a hospital. Additionally, the predictive models may also provide recommendations for a specific patient on their duration length for hospital stay after the procedure.

Finally, as more clinical data is added to the clinical outcome database 62 over time, the model training module 54 may be used to update the machine learning algorithms accordingly in order to reduce predictive error. Thus, this enables the predictive outcome algorithms to continuously learn based upon the input of new data using the tool. Additionally, new parameters may be added in the future and the rank of the existing parameters may be changed to further improve the predictive models from data directly form CT and/or MRI images, for example, bone density, bone architecture, soft tissue tears, and/or other soft tissue damage, such as rotator cuff fatty infiltration, which may further assist the doctor in clinical decision making for treatment and/or outcomes predictions.

In some embodiments, from these images, glenohumeral or other joint bone-to-bone relationships may be assessed, and the patient specific data may influence the predictive models as a new input that further assists in clinical decision making for treatment or outcome predictions. With new data, the predictive models may also be more transferrable and generalizable to other total shoulder arthroplasty systems and perhaps even to other arthroplasty systems for different joints and applications such as spine, hip, knee, ankle, trauma, etc). When the predictive outcome models have a greater accuracy of prediction, better clinical decision making related to the implant type, size, and location may be made and these will result in improved patients and surgeon satisfaction with more realistic expectations of outcomes.

FIG. 37 is a flowchart of an exemplary method 200 for modeling predictive outcomes of arthroplasty surgical procedures in accordance with one or more embodiments of the present disclosure. The method may be performed by the processor 45 of the server 15.

The method 200 may include receiving 210 pre-operative patient specific data for an arthroplasty surgery to be performed on a joint of a patient.

The method 200 may include inputting 220 the pre-operative patient specific data to at least one first machine learning model to determine a first predicted post-operative joint performance data output, where the first predicted post-operative joint performance data output includes at least one first predicted post-operative outcome metric of the joint.

The method 200 may include displaying 230 the first predicted post-operative joint performance data output on a display to a user.

The method 200 may include receiving 240 at least one medical image of the joint obtained from at least one medical imaging procedure performed on the patient.

The method 200 may include generating 250 a reconstruction plan of the joint of the patient based on the at least one medical image of the joint, and at least one arthroplasty surgical parameter obtained from the user in response to the displayed first predicted post-operative joint performance data output where the reconstruction plan includes at least one arthroplasty surgical parameter that is selected from at least one implant, at least one implant size, at least one arthroplasty surgical procedure, at least one position for implanting the at least one implant in the joint, or any combination thereof.

The method 200 may include inputting 260 the at least one arthroplasty surgical parameter into at least one second machine learning model to determine a second predicted post-operative joint performance data output including at least one second predicted post-operative outcome metric of the joint.

The method 200 may include displaying 270 the second predicted post-operative joint performance data output on the display to the user.

The method 200 may include updating 280 the displayed second predicted post-operative joint performance data output to include at least one arthroplasty surgery recommendation, in response to the user varying any of the at least one arthroplasty surgical parameter, before the arthroplasty surgery, during the arthroplasty surgery, or both. This may allow the surgeon 20 to adjust any of the surgical parameters for optimizing any of the predicted post-operative outcome metrics on-the-fly either before surgery and/or during the arthroplasty surgical procedure.

In some embodiments, an apparatus may include a processor and a non-transitory memory storing instructions which, when executed by the processor, cause the processor to:
  receive pre-operative patient specific data for an arthroplasty surgery to be performed on a joint of a patient;
  input the pre-operative patient specific data to at least one machine learning model to determine a first predicted post-operative joint performance data output;
    where the first predicted post-operative joint performance data output may include at least one first predicted post-operative outcome metric of the joint;
  display the first predicted post-operative joint performance data output on a display to a user;
  receive at least one medical image of the joint obtained from at least one medical imaging procedure performed on the patient;
  generate a reconstruction plan of the joint of the patient based on the at least one medical image of the joint, and at least one arthroplasty surgical parameter obtained from the user in response to the displayed first predicted post-operative joint performance data output;
  input the at least one arthroplasty surgical parameter into the at least one machine learning model to determine a second predicted post-operative joint performance data output including at least one second predicted post-operative outcome metric of the joint; and
  display the second predicted post-operative joint performance data output on the display to the user.

In some embodiments, an apparatus may include a processor and a non-transitory memory storing instructions which, when executed by the processor, cause the processor to:
  receive pre-operative patient specific data for an arthroplasty surgery to be performed on a joint of a patient;
    where the pre-operative patient specific data may include:
      (i) a medical history of the patient,
      (ii) a measured range of movement for at least one type of joint movement of the joint, and
      (iii) at least one pain metric associated with the joint;
  input the pre-operative patient specific data to at least one first machine learning model to determine a first predicted post-operative joint performance data output;
    where the first predicted post-operative joint performance data output may include at least one first predicted post-operative outcome metric of the joint;
  display the first predicted post-operative joint performance data output on a display to a user;
  receive at least one medical image of the joint obtained from at least one medical imaging procedure performed on the patient;
  generate a reconstruction plan of the joint of the patient based on the at least one medical image of the joint, and at least one arthroplasty surgical parameter obtained from the user in response to the displayed first predicted post-operative joint performance data output;
    where the reconstruction plan may include the at least one arthroplasty surgical parameter that is selected from:
      (i) at least one implant,
      (ii) at least one implant size,
      (iii) at least one arthroplasty surgical procedure,
      (iv) at least one position for implanting the at least one implant in the joint, or
      (v) any combination thereof;
  input the at least one arthroplasty surgical parameter into at least one second machine learning model to determine a second predicted post-operative joint performance data output including at least one second predicted post-operative outcome metric of the joint;
  display the second predicted post-operative joint performance data output on the display to the user; and
  update the displayed second predicted post-operative joint performance data output to include at least one arthroplasty surgery recommendation, in response to the user varying any of the at least one arthroplasty surgical parameter, before the arthroplasty surgery, during the arthroplasty surgery, or both.

In some embodiments, the processor may be configured to receive the pre-operative patient specific data by receiving the pre-operative patient specific data over a communication network from at least one electronic medical resource.

In some embodiments, the at least one medical image may include at least one of: (a) an X-ray image, (b) a computerized tomography image, (c) a magnetic resonance image, (d) a three-dimensional (3D) image, (e) a 3D medical image generated from multiple X-ray images, (f) a frame of a video, or any combination thereof.

In some embodiments, the at least one first predicted post-operative outcome metric and at least one second predicted post-operative outcome metric may be predicted for at least one of: (a) a number of days, (b) a number of months, and (c) a number of years.

In some embodiments, the processor may be configured to display the second predicted post-operative joint performance data output with recommendations for the at least one arthroplasty surgical parameter.

In some embodiments, the joint may be selected from the group consisting of a hip joint, a knee joint, a shoulder joint, an elbow joint, and an ankle joint.

In some embodiments, the joint may be a shoulder joint.

In some embodiments, the pre-operative patient specific data may include: (a) patient demographics, (b) a patient diagnosis, (c) a patient comorbidity, (d) a patient medical history, (e) a shoulder active range of motion measure, (f) a patient self-reported measure of pain, function, or both, (g) a patient score based on American Shoulder and Elbow Surgeons Shoulder Score (ASES), (h) a patient score based on Constant Shoulder Score (CSS), or any combination thereof.

In some embodiments, the at least one arthroplasty surgical procedure may be selected from the group consisting of an anatomic total shoulder arthroplasty, a reverse total shoulder arthroplasty, deltopectoral technique, and a superior-lateral technique.

In some embodiments, the at least one first predicted post-operative outcome metric and the at least one second predicted post-operative outcome metric may be selected from the group consisting of an American Shoulder and Elbow (ASES) score, a University of California, Los Angeles (UCLA) score, a constant score, a global shoulder function score, a Visual Analogue Scale (VAS) Pain score, a smart shoulder arthroplasty score, an internal rotation (IR) score, an abduction measurement, a forward elevation measurement, and an external rotation measurement.

In some embodiments, a method may include:
receiving, by a processor, pre-operative patient specific data for an arthroplasty surgery to be performed on a joint of a patient;
inputting, by the processor, the pre-operative patient specific data to at least one machine learning model to determine a first predicted post-operative joint performance data output;
where the first predicted post-operative joint performance data output may include at least one first predicted post-operative outcome metric of the joint;
displaying, by the processor, the first predicted post-operative joint performance data output on a display to a user;
receiving, by the processor, at least one medical image of the joint obtained from at least one medical imaging procedure performed on the patient;
generating, by the processor, a reconstruction plan of the joint of the patient based on the at least one medical image of the joint, and at least one arthroplasty surgical parameter obtained from the user in response to the displayed first predicted post-operative joint performance data output;
inputting, by the processor, the reconstruction plan into the at least one machine learning model to determine a second predicted post-operative joint performance data output including at least one second predicted post-operative outcome metric of the joint; and
displaying, by the processor, the second predicted post-operative joint performance data output on the display to the user.

In some embodiments, a method may include:
receiving, by a processor, pre-operative patient specific data for an arthroplasty surgery to be performed on a joint of a patient;
where the pre-operative patient specific data includes:
(i) a medical history of the patient,
(ii) a measured range of movement for at least one type of joint movement of the joint, and
(iii) at least one pain metric associated with the joint;
inputting, by the processor, the pre-operative patient specific data to at least one first machine learning model to determine a first predicted post-operative joint performance data output;
where the first predicted post-operative joint performance data output may include at least one first predicted post-operative outcome metric of the joint;
displaying, by the processor, the first predicted post-operative joint performance data output on a display to a user;
receiving, by the processor, at least one medical image of the joint obtained from at least one medical imaging procedure performed on the patient;
generating, by the processor, a reconstruction plan of the joint of the patient based on the at least one medical image of the joint, and at least one arthroplasty surgical parameter obtained from the user in response to the displayed first predicted post-operative joint performance data output;
where the reconstruction plan may include the at least one arthroplasty surgical parameter that is selected from:
(i) at least one implant,
(ii) at least one implant size,
(iii) at least one arthroplasty surgical procedure,
(iv) at least one position for implanting the at least one implant in the joint, or
(v) any combination thereof;
inputting, by the processor, the reconstruction plan into at least one second machine learning model to determine a second predicted post-operative joint performance data output including at least one second predicted post-operative outcome metric of the joint;
displaying, by the processor, the second predicted post-operative joint performance data output on the display to the user; and
updating, by the processor, the displayed second predicted post-operative joint performance data output to include at least one arthroplasty surgery recommendation, in response to the user varying any of the at least one arthroplasty surgical parameter in the reconstruction plan, before the arthroplasty surgery, during the arthroplasty surgery, or both.

In some embodiments, receiving the pre-operative patient specific data may include receiving the pre-operative patient specific data over a communication network from at least one electronic medical resource.

In some embodiments, the at least one medical image may include at least one of: (a) an X-ray image, (b) a computerized tomography image, (c) a magnetic resonance image, (d) a three-dimensional (3D) image, (e) a 3D medical image generated from multiple X-ray images, (f) a frame of a video, or any combination thereof.

In some embodiments, the at least one first predicted post-operative outcome metric and at least one second predicted post-operative outcome metric may be predicted for at least one of: (a) a number of days, (b) a number of months, and (c) a number of years.

In some embodiments, displaying the second predicted post-operative joint performance data output may include displaying the second predicted post-operative joint performance data output with recommendations for the at least one arthroplasty surgical parameter.

In some embodiments, the joint may be selected from the group consisting of a hip joint, a knee joint, a shoulder joint, an elbow joint, and an ankle joint.

In some embodiments, the joint may be a shoulder joint.

In some embodiments, the pre-operative patient specific data may include: (a) patient demographics, (b) a patient diagnosis, (c) a patient comorbidity, (d) a patient medical history, (e) a shoulder active range of motion measure, (f) a patient self-reported measure of pain, function, or both, (g) a patient score based on American Shoulder and Elbow Surgeons Shoulder Score (ASES), (h) a patient score based on Constant Shoulder Score (CSS), a shoulder arthroplasty smart score, or any combination thereof.

In some embodiments, the at least one arthroplasty surgical procedure may be selected from the group consisting of an anatomic total shoulder arthroplasty, a reverse total shoulder arthroplasty, deltopectoral technique, and a superior-lateral technique.

In some embodiments, the at least one first predicted post-operative outcome metric and the at least one second predicted post-operative outcome metric may be selected from the group consisting of an American Shoulder and Elbow (ASES) score, a University of California, Los Angeles (UCLA) score, a constant score, a global shoulder function score, a Visual Analogue Scale (VAS) Pain score, a smart shoulder arthroplasty score, an internal rotation (IR) score, an abduction measurement, a forward elevation measurement, and an external rotation measurement.

In some embodiments, exemplary inventive, specially programmed computing systems/platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, WiFi, WiMax, CDMA, satellite, ZigBee, and other suitable communication modes. In some embodiments, the NFC can represent a short-range wireless communications technology in which NFC-enabled devices are "swiped," "bumped," "tap" or otherwise moved in close proximity to communicate. In some embodiments, the NFC could include a set of short-range wireless technologies, typically requiring a distance of 10 cm or less. In some embodiments, the NFC may operate at 13.56 MHz on ISO/IEC 18000-3 air interface and at rates ranging from 106 kbit/s to 424 kbit/s. In some embodiments, the NFC can involve an initiator and a target; the initiator actively generates an RF field that can power a passive target. In some embodiments, this can enable NFC targets to take very simple form factors such as tags, stickers, key fobs, or cards that do not require batteries. In some embodiments, the NFC's peer-to-peer communication can be conducted when a plurality of NFC-enable devices (e.g., smartphones) within close proximity of each other.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of exemplary inventive computer-based systems/platforms, exemplary inventive computer-based devices, and/or exemplary inventive computer-based components of the present disclosure such as the computing device 77 may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of exemplary inventive computer-based systems/platforms, exemplary inventive computer-based devices, and/or exemplary inventive computer-based components of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a social media post, a map, an entire application (e.g., a calculator), etc. In some embodiments, as detailed herein, one or more of exemplary inventive computer-based systems/platforms, exemplary inventive computer-based devices, and/or exemplary inventive computer-based components of the present disclosure may be implemented across one or more of various computer platforms such as, but not limited to: (1) FreeBSD, NetBSD, OpenBSD; (2) Linux; (3) Microsoft Windows; (4) OS X (MacOS); (5) MacOS 11; (6) Solaris; (7) Android; (8) iOS; (9) Embedded Linux; (10) Tizen; (11) WebOS; (12) IBM i; (13) IBM AIX; (14) Binary Runtime Environment for Wireless (BREW); (15) Cocoa (API); (16) Cocoa Touch; (17) Java Platforms; (18) JavaFX; (19) JavaFX Mobile; (20) Microsoft DirectX; (21) .NET Framework; (22) Silverlight; (23) Open Web Platform; (24) Oracle Database; (25) Qt; (26) Eclipse Rich Client Platform; (27) SAP NetWeaver; (28) Smartface; and/or (29) Windows Runtime.

In some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, exemplary inventive computer-based systems/platforms, exemplary inventive computer-based devices, and/or exemplary inventive computer-based components of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, exemplary inventive computer-based systems/platforms, exemplary inventive computer-based devices, and/or exemplary inventive computer-based components of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, and/or objects. For example, such projections may be a visual overlay for a mobile augmented reality (MAR) application.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the exemplary inventive computer-based systems/platforms, the exemplary inventive computer-based devices, and/or the exemplary inventive computer-based components of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTRO, SHA-1, SHA-2, Tiger (TTH), WHIRLPOOL, RNGs).

The aforementioned examples are, of course, illustrative and not restrictive.

As used herein, the term "user" shall have a meaning of at least one user. In the context as used herein, the user may be a doctor, or a surgeon or someone acting on behalf of the doctor, or surgeon, a laboratory technician, surgical staff, and the like.

In some embodiments, the exemplary inventive computer-based systems/platforms, the exemplary inventive computer-based devices, and/or the exemplary inventive computer-based components of the present disclosure may be configured to utilize one or more exemplary AI/machine learning techniques chosen from, but not limited to, decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net) or other suitable network. In some embodiments and, optionally, in combination of any embodiment described above or below, an exemplary implementation of Neural Network may be executed as follows:

i) Define Neural Network architecture/model,
ii) Transfer the input data to the exemplary neural network model,
iii) Train the exemplary model incrementally,
iv) determine the accuracy for a specific number of timesteps,
v) apply the exemplary trained model to process the newly-received input data,
vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values/functions and/or aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

The disclosure described herein may be practiced in the absence of any element or elements, limitation or limitations, which is not specifically disclosed herein. Thus, for example, in each instance herein, any of the terms "comprising," "consisting essentially of and "consisting of" may be replaced with either of the other two terms, without altering their respective meanings as defined herein. The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure.

The invention claimed is:
1. An apparatus, comprising:
a processor;
a display; and
a non-transitory memory storing instructions which, when executed by the processor, cause the processor to:
receive pre-operative patient specific data for an arthroplasty surgery to be performed on a joint of a patient;
wherein the pre-operative patient specific data comprises:
(i) a medical history of the patient,
(ii) a measured range of movement for at least one type of joint movement of the joint, and
(iii) at least one pain metric associated with the joint;
input the pre-operative patient specific data to at least one first machine learning model to determine a first predicted post-operative joint performance data output at a plurality of first post-operative timepoints after surgery;
wherein the first predicted post-operative joint performance data output comprises at least:
(i) a first predicted range of movement for at least one type of joint movement of the joint, and
(ii) at least one first predicted pain metric associated with the joint;
wherein the at least one first machine learning model is trained to output data comprising a plurality of first values for the first predicted post-operative joint performance data output at the plurality of first post-operative timepoints after surgery, each first value is at each particular first timepoint of the plurality of first post-operative timepoints after surgery;
wherein input data to train the at least one first machine learning model comprises at least the pre-operative patient specific data;
display the first predicted post-operative joint performance data output on the display to a user as a displayed first predicted post-operative joint performance data output;
receive at least one medical image of the joint obtained from at least one medical imaging procedure performed on the patient;
receive, from the user, at least one arthroplasty surgical parameter based on the displayed first predicted post-operative joint performance data output;
wherein the at least one arthroplasty surgical parameter is selected from:
(i) at least one implant,
(ii) at least one implant size,
(iii) at least one arthroplasty surgical procedure,
(iv) at least one position for implanting the at least one implant in the joint, or
(v) any combination thereof;
generate a reconstruction plan of the joint of the patient based at least in part on the at least one medical image of the joint and the at least one arthroplasty surgical parameter,
input the pre-operative patient specific data and reconstruction plan data into at least one second machine learning model to determine a second predicted post-operative joint performance data output at a plurality of second post-operative timepoints after surgery;
wherein the second predicted post-operative joint performance data output comprises at least:
(i) a second predicted range of movement for at least one type of joint movement of the joint, and
(ii) at least one second predicted pain metric associated with the joint;
wherein the at least one second machine learning model is trained to output data comprising a plurality of second values for the second predicted post-operative joint performance data output at the plurality of second post-operative timepoints after surgery, each second value is at a particular second timepoint of the plurality of second post-operative timepoints after surgery;

wherein input data to train the at least one second machine learning model comprises at least:
(i) the pre-operative patient specific data, and
(ii) the reconstruction plan data;
display the reconstruction plan data and the second predicted post-operative joint performance data output at the plurality of second post-operative timepoints after surgery on the display to the user; and
update the second predicted post-operative joint performance data output determined from the at least one second machine learning model in response to the user varying any parameter of the reconstruction plan data inputted into the at least one second machine learning model, before the arthroplasty surgery, during the arthroplasty surgery, or both.

2. The apparatus of claim 1, wherein the processor is configured to receive the pre-operative patient specific data by receiving the pre-operative patient specific data over a communication network from at least one electronic medical resource.

3. The apparatus of claim 1, wherein the at least one medical image comprises at least one of: (a) an X-ray image, (b) a computerized tomography image, (c) a magnetic resonance image, (d) a three-dimensional (3D) image, (e) a 3D medical image generated from multiple X-ray images, (f) a frame of a video, or any combination thereof.

4. The apparatus of claim 1, wherein the at least one first predicted post-operative joint performance data at the plurality of first post-operative timepoints after surgery and the at least one second predicted post-operative joint performance data at the plurality of second post-operative timepoints after surgery are predicted for at least one of: (a) a number of days, (b) a number of months, and (c) a number of years.

5. The apparatus of claim 1, wherein the processor is configured to display the second predicted post-operative joint performance data output with recommendations for the at least one arthroplasty surgical parameter.

6. The apparatus according to claim 1, wherein the joint is selected from the group consisting of a hip joint, a knee joint, a shoulder joint, an elbow joint, and an ankle joint.

7. The apparatus according to claim 1, wherein the processor is further configured to determine from the at least one second machine learning model, at least one arthroplasty surgery recommendation to display to the user on the display.

8. The apparatus according to claim 1, wherein the joint is a shoulder joint.

9. The apparatus of claim 8, wherein the pre-operative patient specific data comprises: (a) patient demographics, (b) a patient diagnosis, (c) a patient comorbidity, (d) a patient medical history, (e) a shoulder active range of motion measure, (f) a patient self-reported measure of pain, function, or both, (g) a patient score based on American Shoulder and Elbow Surgeons Shoulder Score (ASES), (h) a patient score based on Constant Shoulder Score (CSS), or any combination thereof.

10. The apparatus of claim 8, wherein the at least one arthroplasty surgical procedure is selected from the group consisting of an anatomic total shoulder arthroplasty, a reverse total shoulder arthroplasty, deltopectoral technique, and a superior-lateral technique.

11. The apparatus of claim 8, wherein the at least one first predicted post-operative joint performance data at the plurality of first post-operative timepoints after surgery and the at least one second predicted post-operative joint performance data at the plurality of first post-operative timepoints after surgery are is selected from the group consisting of an American Shoulder and Elbow (ASES) score, a University of California, Los Angeles (UCLA) patient reported outcome measures score, a constant score, a global shoulder function score, a Visual Analogue Scale (VAS) Pain score, an abduction score, a forward elevation score, and an external rotation score.

12. A method, comprising:
receiving, by a processor, pre-operative patient specific data for an arthroplasty surgery to be performed on a joint of a patient;
wherein the pre-operative patient specific data comprises:
(i) a medical history of the patient,
(ii) a measured range of movement for at least one type of joint movement of the joint, and
(iii) at least one pain metric associated with the joint;
inputting, by the processor, the pre-operative patient specific data to at least one first machine learning model to determine a first predicted post-operative joint performance data output at a plurality of post-operative timepoints after surgery;
wherein the first predicted post-operative joint performance data output comprises at least:
(i) a predicted range of movement for at least one type of joint movement of the joint, and
at least one first predicted pain metric associated with the joint;
wherein the at least one first machine learning model is trained to output data comprising a plurality of first values for the first predicted post-operative joint performance data output at the plurality of first post-operative timepoints after surgery, each first value is at each particular first timepoint of the plurality of first post-operative timepoints after surgery;
displaying, by the processor, the first predicted post-operative joint performance data output on a display to a user as a displayed first predicted post-operative joint performance data output;
receiving, by the processor, at least one medical image of the joint obtained from at least one medical imaging procedure performed on the patient;
wherein the at least one arthroplasty surgical parameter is selected from:
(i) at least one implant,
(ii) at least one implant size,
(iii) at least one arthroplasty surgical procedure,
(iv) at least one position for implanting the at least one implant in the joint, or
(v) any combination thereof;
generating, by the processor, a reconstruction plan of the joint of the patient based at least in part on the at least one medical image of the joint and the at least one arthroplasty surgical parameter;
inputting, by the processor, the pre-operative patient specific data and reconstruction plan data into at least one second machine learning model to determine a second predicted post-operative joint performance data output at a plurality of second post-operative timepoints after surgery;
wherein the second predicted post-operative joint performance data output comprises at least:
(i) a second predicted range of movement for at least one type of joint movement of the joint, and
(ii) at least one second predicted pain metric associated with the joint;

wherein the at least one second machine learning model is trained to output data comprising a plurality of second values for the second predicted post-operative joint performance data at the plurality of second post-operative timepoints after surgery, each second value is at a particular second timepoint of the plurality of second post-operative timepoints after surgery;

wherein input data to train the at least one second machine learning model comprises at least:
(i) the pre-operative patient specific data, and
(ii) the reconstruction plan data;

displaying, by the processor, the reconstruction plan data and the second predicted post-operative joint performance data output at the plurality of second post-operative timepoints after surgery on the display to the user; and updating, by the processor, the second predicted post-operative joint performance data output determined from the at least one second machine learning model in response to the user varying any parameter of the reconstruction plan data inputted into the at least one second machine learning model, before the arthroplasty surgery, during the arthroplasty surgery, or both.

13. The method of claim 12, wherein receiving the pre-operative patient specific data comprises receiving the pre-operative patient specific data over a communication network from at least one electronic medical resource.

14. The method of claim 12, wherein the at least one medical image comprises at least one of: (a) an X-ray image, (b) a computerized tomography image, (c) a magnetic resonance image, (d) a three-dimensional (3D) image, (e) a 3D medical image generated from multiple X-ray images, (f) a frame of a video, or any combination thereof.

15. The method of claim 12, wherein the at least one first predicted post-operative joint performance data at the plurality of first post-operative timepoints after surgery and the at least one second predicted post-operative joint performance data at the plurality of second post-operative timepoints after surgery are predicted for at least one of: (a) a number of days, (b) a number of months, and (c) a number of years.

16. The method of claim 12, wherein displaying the second predicted post-operative joint performance data output comprises displaying the second predicted post-operative joint performance data output with recommendations for the at least one arthroplasty surgical parameter.

17. The method of claim 12, wherein the joint is selected from the group consisting of a hip joint, a knee joint, a shoulder joint, an elbow joint, and an ankle joint.

18. The method according to claim 12, further comprising determining, by the processor, from the at least one second machine learning model, at least one arthroplasty surgery recommendation to display to the user on the display.

19. The method of claim 12, wherein the joint is a shoulder joint.

20. The method of claim 19, wherein the pre-operative patient specific data comprises: (a) patient demographics, (b) a patient diagnosis, (c) a patient comorbidity, (d) a patient medical history, (e) a shoulder active range of motion measure, (f) a patient self-reported measure of pain, function, or both, (g) a patient score based on American Shoulder and Elbow Surgeons Shoulder Score (ASES), (h) a patient score based on Constant Shoulder Score (CSS), or any combination thereof.

21. The method of claim 19, wherein the at least one arthroplasty surgical procedure is selected from the group consisting of an anatomic total shoulder arthroplasty, a reverse total shoulder arthroplasty, deltopectoral technique, and a superior-lateral technique.

22. The method of claim 19, wherein the at least one first predicted post-operative joint performance data at the plurality of first post-operative timepoints after surgery and the at least one second predicted post-operative joint performance data at the plurality of first post-operative timepoints after surgery are is selected from the group consisting of an American Shoulder and Elbow (ASES) score, a University of California, Los Angeles (UCLA) patient reported outcome measures score, a constant score, a global shoulder function score, a Visual Analogue Scale (VAS) Pain score, an abduction score, a forward elevation score, and an external rotation score.

* * * * *